United States Patent
Tang et al.

(10) Patent No.: US 11,192,954 B2
(45) Date of Patent: Dec. 7, 2021

(54) COMPOUNDS AND METHODS FOR THE TREATMENT OF TROP2 POSITIVE DISEASES

(71) Applicant: BIO-THERA SOLUTIONS, LTD., Science City (CN)

(72) Inventors: Weijia Tang, Science City (CN); Xiaoyang Huang, Science City (CN); Jin-Chen Yu, Science City (CN); Ziqiang Ou, Science City (CN); Xian Peng, Science City (CN); Yili Yang, Science City (CN); Shengfeng Li, Science City (CN); Chao Qin, Science City (CN)

(73) Assignee: Bio-Thera Solutions, Ltd., Guangzhou (CN)

( * ) Notice: Subject to any disclaimer, the term of this patent is extended or adjusted under 35 U.S.C. 154(b) by 519 days.

(21) Appl. No.: 16/100,995

(22) Filed: Aug. 10, 2018

(65) Prior Publication Data

US 2019/0048095 A1 Feb. 14, 2019

(30) Foreign Application Priority Data

Aug. 11, 2017 (CN) .......................... 201710687161.6

(51) Int. Cl.
*C07K 16/30* (2006.01)
*A61K 47/68* (2017.01)
*A61P 35/00* (2006.01)
*A61K 39/00* (2006.01)

(52) U.S. Cl.
CPC .......... *C07K 16/30* (2013.01); *A61K 47/6801* (2017.08); *A61K 47/6803* (2017.08); *A61K 47/6851* (2017.08); *A61P 35/00* (2018.01); *A61K 2039/507* (2013.01); *C07K 2317/73* (2013.01); *C07K 2317/732* (2013.01)

(58) Field of Classification Search
CPC ........ A61K 39/39533; A61K 39/39558; A61K 2039/505; A61K 2039/507; A61K 47/6801; A61K 47/6803; A61K 47/6819; A61K 47/6851; C07K 2317/73; C07K 2317/732; C07K 16/30; C07K 2317/56
See application file for complete search history.

(56) References Cited

U.S. PATENT DOCUMENTS

| | | | |
|---|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,256,746 A | 3/1981 | Miyashita et al. |
| 4,260,608 A | 4/1981 | Miyashita et al. |
| 4,294,757 A | 10/1981 | Asai et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,938,949 A | 7/1990 | Borch et al. |
| 5,639,641 A | 6/1997 | Pedersen et al. |
| 5,885,793 A | 3/1999 | Griffiths et al. |
| 5,969,108 A | 10/1999 | McCafferty et al. |
| 7,195,595 B2 | 3/2007 | Ling et al. |
| 9,833,511 B2 | 12/2017 | Govindan et al. |
| 9,850,312 B2 | 12/2017 | Agatsuma et al. |
| 2014/0377287 A1* | 12/2014 | Govindan .......... A61K 51/1051 424/178.1 |

FOREIGN PATENT DOCUMENTS

| | | | |
|---|---|---|---|
| WO | 92/01047 A1 | 1/1992 |
| WO | 99/06587 A2 | 2/1999 |
| WO | WO-2014094353 A1 * | 6/2014 | ............. A61P 35/02 |
| WO | 2016/040825 A1 | 3/2016 |
| WO | 2016/040856 A2 | 3/2016 |
| WO | 2017/068511 A1 | 4/2017 |

OTHER PUBLICATIONS

Abstract of Hamid et al (Journal of Clinical Oncology, 2015, vol. 33, No. 15, suppl, abstract No. TPS3087 (Year: 2015).*
Sigdel et al, Proteomics Clin. Appl. 2010, vol. 4, pp. 32-47 (Year: 2010).*
Liu et al, Respiratory Research, 2016, vol. 17, p. 159, 14 pages (Year: 2016).*
G. Calabrese et al., Assignment1 of TACSTD1 (alias TROP1, M4S1) to human chromosome 2p21 and refinement of mapping of TACSTD2 (alias TROP2, M1S1) to human chromosome 1p32 by in situ hybridization, Cytogenetics and Cell Genetics, 92:164-165 (2001).
M. Lipinski et al., Human trophoblast cell-surface antigens defined by monoclonal antibodies, Proceedings of the National Academy of Sciences of the USA, vol. 78(8):5147-5150 (1981).
E. Guerra et al., The Trop-2 signalling network in cancer growth, Oncogene, 32:1594-1600 (2013).
A. McDougall et al., Trop2: From Development to Disease, Developmental Dynamics, 244:99-109 (2015).
L. Stepan et al., Expression of Trop2 Cell Surface Glycoprotein in Normal and Tumor Tissues: Potential Implications as a Cancer Therapeutic Target, Journal of Histochemistry & Cytochemistry, 59(7):701-710 (2011).
M. Tretotola et al., Upregulation of Trop-2 quantitatively stimulates human cancer growth, Oncogene 32:222-233 (2013).

(Continued)

*Primary Examiner* — Karen A. Canella
(74) *Attorney, Agent, or Firm* — Buchanan Ingersoll & Rooney PC

(57) ABSTRACT

The present invention generally relates to compounds comprising antibodies, antigen-binding fragments thereof, polypeptides, and immunoconjugates that bind to TROP2 (TAC-STD2). The present invention also relates to methods of using such TROP2-binding molecules for diagnosing and treating diseases, such as malignancies.

18 Claims, 19 Drawing Sheets

Specification includes a Sequence Listing.

(56) References Cited

OTHER PUBLICATIONS

A. Goldstein et al., Trop2 identifies a subpopulation of murine and human prostate basal cells with stem cell characteristics, Proceedings of the National Academy of Sciences of the USA, 105(52):20882-20887 (2008).
F. Ambrogi et al., Trop-2 Is a Determinant of Breast Cancer Survival, PLoS One, 9(5):1-11 (2014).
T. Liu et al., Overexpression of TROP2 Predicts Poor Prognosis of Patients with Cervical Cancer and Promotes the Proliferation and Invasion of Cervical Cancer Cells by Regulating ERK Signaling Pathway, PLoS One, 8(9):1-14 (2013).
T. Ohmachi et al., Clinical Significance of TROP2 Expression in Colorectal Cancer, Clinical Cancer Research, 12(10):3057-3063 (2006).
D. Goldenberg et al., Trop-2 is a novel target for solid cancer therapy with sacituzumab govitecan (IMMU-132), an antibody-drug conjugate (ADC), Oncotarget, 6:22496-22512 (2015).
T. Cardillo et al., Humanized Anti-Trop-2 IgG-SN-38 Conjugate for Effective Treatment of Diverse Epithelial Cancers: Preclinical Studies in Human Cancer Xenograft Models and Monkeys, Clinical Cancer Research, 17(10):3157-3169 (2011).
A. Ocean, MD et al., Sacituzumab Govitecan (IMMU-132), an Anti-Trop-2-SN-38 Antibody-Drug Conjugate for the Treatment of Diverse Epithelial Cancers: Safety and Pharmacokinetics, Cancer, DOI: 10.1002/cncr.30789 (May 2017).
S. Remillard et al., Antimitotic Activity of the Potent Tumor Inhibitor Maytansine, Science, 189:1002-1005 (1975).
S. M. Kupchan et al., Maytansine, a Novel Antileukemic Ansa Macrolide from Maytenus ovatus, Journal of the American Chemical Society, 94(4):1354-1356 (1972).
J. Cassady et al., Recent Developments in the Maytansinoid Antitumor Agents, Chemical and Pharmaceutical Bulletin, 52(1):1-26 (2004).
M. Wolpert-DeFilippes et al., Initial Studies on Maytansine-Induced Metaphase Arrest in L1210 Murine Leukemia Cells, Biochemical Pharmacology, 24:1735-1738 (1975).
A. Kawai et al., Chemical Modification of Ansamitocins. III. Synthesis and Biological Effets of 3-Acyl Esters of Maytansinol, Chemical and Pharmaceutical Bulletin, 32(9):3441-3451 (1984).
W. Widdison et al., Semisynthetic Maytansine Analogues for the Targeted Treatment of Cancer, Journal of Medicinal Chemistry, 49(14):4392-4408 (2006).
B. Issell et al., Maytansine, Cancer Treatment Reviews, 5:199-207 (1978).
T. Yu et al., The biosynthetic gene cluster of the maytansinoid antitumor agent ansamitocin from Actinosynnema pretiosum, Proceedings of the National Academy of Sciences of the USA, 99(12):7968-7973 (2002).
Chang et al., "Combining ABCG2 Inhibitors with IMMU-132, an Anti-Trop-2 Antibody Conjugate of SN-38, Overcomes Resistance to SN-38 in Breast and Gastric Cancers", Molecular Cancer Therapeutics, Aug. 2016, pp. 1910-1919, vol. 15, No. 8.
Office Action (Communication) dated Mar. 23, 2021, by the European Patent Office in corresponding European Patent Application No. 18793551.5. (7 pages).

\* cited by examiner

```
GACATCCAGCTGACACAGAGCCCTAGCTCTCTGAGCGCTAGCGTGGGAGATAGGGTGTCCATCACTTGCAAGGCCAGCCA    80
 D  I  Q  L  T  Q  S  P  S  S  L  S  A  S  V  G  D  R  V  S  I  T  C  K  A  S  Q

GGACGTGTCCATCGCAGTGGCTTGGTACCAGCAGAAGCCCGGAAAGGCCCCTAAGCTGCTGATCTACAGCGCCAGCTACA   160
 D  V  S  I  A  V  A  W  Y  Q  Q  K  P  G  K  A  P  K  L  L  I  Y  S  A  S  Y

GATACACCGGAGTGCCAGACAGATTCAGCGGAAGCGGAAGCGGCACAGACTTCACCCTGACCATCAGCAGCCTGCAGCCA   240
 R  Y  T  G  V  P  D  R  F  S  G  S  G  S  G  T  D  F  T  L  T  I  S  S  L  Q  P

GAGGACTTCGCCGTCTACTACTGCCAGCAGCACTACATCACCCCCCTGACCTTCGGAGCCGGAACCAAGGTGGAGATCAA   320
 E  D  F  A  V  Y  Y  C  Q  Q  H  Y  I  T  P  L  T  F  G  A  G  T  K  V  E  I  K

ACGTACGGTGGCTGCACCATCTGTCTTCATCTTCCCGCCATCTGATGAGCAGTTGAAATCTGGAACTGCCTCTGTTGTGT   400
 R  T  V  A  A  P  S  V  F  I  F  P  P  S  D  E  Q  L  K  S  G  T  A  S  V  V

GCCTGCTGAATAACTTCTATCCCAGAGAGGCCAAAGTACAGTGGAAGGTGGATAACGCCCTCCAATCGGGTAACTCCCAG   480
 C  L  L  N  N  F  Y  P  R  E  A  K  V  Q  W  K  V  D  N  A  L  Q  S  G  N  S  Q

GAGAGTGTCACAGAGCAGGACAGCAAGGACAGCACCTACAGCCTCAGCAGCACCCTGACGCTGAGCAAAGCAGACTACGA   560
 E  S  V  T  E  Q  D  S  K  D  S  T  Y  S  L  S  S  T  L  T  L  S  K  A  D  Y  E

GAAACACAAAGTCTACGCCTGCGAAGTCACCCATCAGGGCCTGAGCTCGCCCGTCACAAAGAGCTTCAACAGGGGAGAGT   640
 K  H  K  V  Y  A  C  E  V  T  H  Q  G  L  S  S  P  V  T  K  S  F  N  R  G  E

GTTGA                                                                             645
 C  .
```

FIG. 17A

```
CAGGTGCAGCTGCAGCAGAGCGGATCAGAGCTGAAGAAGCCCGGAGCCAGCGTGAAAGTGTCTTGCAAGG    70
 Q  V  Q  L  Q  Q  S  G  S  E  L  K  K  P  G  A  S  V  K  V  S  C  K

CCAGCGGCTACACCTTCACCAACTACGGCATGAATTGGGTGAAGCAGGCCCCAGGACAGGGACTCAAGTG   140
 P  S  G  Y  T  F  T  N  Y  G  M  N  W  V  K  Q  A  P  G  Q  G  L  K  W

GATGGGTTGGATCAACACCTACACCGGCGAGCCTACATACACCGACGACTTCAAGGGCCGCTTCGCTTTC   210
 M  G  W  I  N  T  Y  T  G  E  P  T  Y  T  D  D  F  K  G  R  F  A  F

AGCCTGGATACCAGCGTGTCCACCGCTTACCTGCAGATCAGCAGCCTGAAGGCCGACGATACAGCCGTGT   280
 S  L  D  T  S  V  S  T  A  Y  L  Q  I  S  S  L  K  A  D  D  T  A  V

ACTTTTGCGCCAGAGGAGGCTTCGGCAGCAGCTACTGGTACTTCGACGTGTGGGGCCAGGGTACCCTGGT   350
 Y  F  C  A  R  G  G  F  G  S  S  Y  W  Y  F  D  V  W  G  Q  G  T  L  V

TACCGTTAGCAGCGCGAGCACCAAGGGCCCGAGCGTGTTTCCGCTGGCTCCGAGCAGCAAAAGCACCAGC   420
 T  V  S  S  A  S  T  K  G  P  S  V  F  P  L  A  P  S  S  K  S  T  S

GGTGGCACCGCAGCGCTGGGTTGCCTGGTGAAAGATTATTTCCCGGAACCGGTGACGGTGTCGTGGAACT   490
 G  G  T  A  A  L  G  C  L  V  K  D  Y  F  P  E  P  V  T  V  S  W  N

CAGGCGCCCTGACCAGCGGCGTGCACACCTTCCCGGCTGTCCTACAGTCCTCAGGACTCTACTCCCTCAG   560
 S  G  A  L  T  S  G  V  H  T  F  P  A  V  L  Q  S  S  G  L  Y  S  L  S

CAGCGTGGTGACCGTGCCCTCCAGCAGCTTGGGCACCCAGACCTACATCTGCAACGTGAATCACAAGCCC   630
 S  V  V  T  V  P  S  S  S  L  G  T  Q  T  Y  I  C  N  V  N  H  K  P

AGCAACACCAAGGTGGACAAGAAAGTTGAGCCCAAATCTTGTGACAAAACTCACACATGCCCACCGTGCC   700
 S  N  T  K  V  D  K  K  V  E  P  K  S  C  D  K  T  H  T  C  P  P  C

CAGCACCTGAACTCCTGGGGGGACCGTCAGTCTTCCTCTTCCCCCCAAAACCCAAGGACACCCTCATGAT   770
 P  A  P  E  L  L  G  G  P  S  V  F  L  F  P  P  K  P  K  D  T  L  M  I

CTCCCGGACCCCTGAGGTCACATGCGTGGTGGTGGACGTGAGCCACGAAGACCCTGAGGTCAAGTTCAAC   840
 S  R  T  P  E  V  T  C  V  V  V  D  V  S  H  E  D  P  E  V  K  F  N

TGGTACGTGGACGGCGTGGAGGTGCATAATGCCAAGACAAAGCCGCGGGAGGAGCAGTACAACAGCACGT   910
 W  Y  V  D  G  V  E  V  H  N  A  K  T  K  P  R  E  E  Q  Y  N  S  T

ACCGGGTGGTCAGCGTCCTCACCGTCCTGCACCAGGACTGGCTGAATGGCAAGGAGTACAAGTGCAAGGT   980
 Y  R  V  V  S  V  L  T  V  L  H  Q  D  W  L  N  G  K  E  Y  K  C  K  V

CTCCAACAAAGCCCTCCCAGCCCCCATCGAGAAAACCATCTCCAAAGCCAAAGGGCAGCCCCGAGAACCA  1050
 S  N  K  A  L  P  A  P  I  E  K  T  I  S  K  A  K  G  Q  P  R  E  P

CAGGTGTACACCCTGCCCCCATCCCGGGATGAGCTGACCAAGAACCAGGTCAGCCTGACCTGCCTGGTCA  1120
 Q  V  Y  T  L  P  P  S  R  D  E  L  T  K  N  Q  V  S  L  T  C  L  V

AAGGCTTCTATCCCAGCGACATCGCCGTGGAGTGGGAGAGCAATGGGCAGCCGGAGAACAACTACAAGAC  1190
 K  G  F  Y  P  S  D  I  A  V  E  W  E  S  N  G  Q  P  E  N  N  Y  K  T

CACGCCTCCCGTGCTGGACTCCGACGGCTCCTTCTTCCTCTACAGCAAGCTCACCGTGGACAAGAGCAGG  1260
 T  P  P  V  L  D  S  D  G  S  F  F  L  Y  S  K  L  T  V  D  K  S  R

TGGCAGCAGGGGAACGTCTTCTCATGCTCCGTGATGCATGAGGCTCTGCACAACCACTACACGCAGAAGA  1330
 W  Q  Q  G  N  V  F  S  C  S  V  M  H  E  A  L  H  N  H  Y  T  Q  K

GCCTCTCCCTGTCTCCGGGTAAATGA                                              1356
 S  L  S  L  S  P  G  K  .
```

FIG. 17B

```
GACATCCAGCTGACACAGAGCCCTAGCTCTCTGAGCGCTAGCGTGGGAGATAGGGTGTCCATCACTTGCA     70
 D  I  Q  L  T  Q  S  P  S  S  L  S  A  S  V  G  D  R  V  S  I  T  C

AGGCCAGCCAGGACGTGTCCATCGCAGTGGCTTGGTACCAGCAGAAGCCCGGAAAGGCCCCTAAGCTGCT    140
 R  A  S  Q  D  V  S  I  A  V  A  W  Y  Q  Q  K  P  G  K  A  P  K  L  L

GATCTACAGCGCCAGCTACAGATACACCGGAGTGCCAGACAGATTCAGCGGAAGCGGAAGCGGCACAGAC    210
 I  Y  S  A  S  Y  R  Y  T  G  V  P  D  R  F  S  G  S  G  S  G  T  D

TTCACCCTGACCATCAGCAGCCTGCAGCCAGAGGACTTCGCCGTCTACTACTGCCAGCAGCACTACATCA    280
 F  T  L  T  I  S  S  L  Q  P  E  D  F  A  V  Y  Y  C  Q  Q  H  Y  I

CCCCCCTGACCTTCGGAGCCGGAACCAAGGTGGAGATCAAACGTACGGTGGCTGCACCATCTGTCTTCAT    350
 T  P  L  T  F  G  A  G  T  K  V  E  I  K  R  T  V  A  A  P  S  V  F  I

CTTCCCGCCATCTGATGAGCAGTTGAAATCTGGAACTGCCTCTGTTGTGTGCCTGCTGAATAACTTCTAT    420
 F  P  P  S  D  E  Q  L  K  S  G  T  A  S  V  V  C  L  L  N  N  F  Y

CCCAGAGAGGCCAAAGTACAGTGGAAGGTGGATAACGCCCTCCAATCGGGTAACTCCCAGGAGAGTGTCA    490
 P  R  E  A  K  V  Q  W  K  V  D  N  A  L  Q  S  G  N  S  Q  E  S  V

CAGAGCAGGACAGCAAGGACAGCACCTACAGCCTCAGCAGCACCCTGACGCTGAGCAAAGCAGACTACGA    560
 T  E  Q  D  S  K  D  S  T  Y  S  L  S  S  T  L  T  L  S  K  A  D  Y  E

GAAACACAAAGTCTACGCCTGCGAAGTCACCCATCAGGGCCTGAGCTCGCCCGTCACAAAGAGCTTCAAC    630
 K  H  K  V  Y  A  C  E  V  T  H  Q  G  L  S  S  P  V  T  K  S  F  N

AGGGGAGAGTGTTGA                                                          645
 R  G  E  C  .
```

FIG. 18A

```
CAGGTGCAGCTGCAGCAGAGCGGATCAGAGCTGAAGAAGCCCGGAGCCAGCGTGAAAGTGTCTTGCAAGG    70
 Q  V  Q  L  Q  Q  S  G  S  E  L  K  K  P  G  A  S  V  K  V  S  C  K

CCAGCGGCTACACCTTCACCAACTACGGCATGAATTGGGTGAAGCAGGCCCCAGGACAGGGACTCAAGTG   140
 A  S  G  Y  T  F  T  N  Y  G  M  N  W  V  K  Q  A  P  G  Q  G  L  K  W

GATGGGTTGGATCAACACCTACACCGGCGAGCCTACATACACCGACGACTTCAAGGGCCGCTTCGCTTTC   210
 M  G  W  I  N  T  Y  T  G  E  P  T  Y  T  D  D  F  K  G  R  F  A  F

AGCCTGGATACCAGCGTGTCCACCGCTTACCTGCAGATCAGCAGCCTGAAGGCCGACGATACAGCCGTGT   280
 S  L  D  T  S  V  S  T  A  Y  L  Q  I  S  S  L  K  A  D  D  T  A  V

ACTTTTGCGCCAGAGGAGGCTTCGGCAGCAGCTACTGGTACTTCGACGTGTGGGGCAGGGTACCCTGGT   350
 Y  F  C  A  R  G  G  F  G  S  S  Y  W  Y  F  D  V  W  G  Q  G  T  L  V

TACCGTTAGCAGCTGTAGCACCAAAGGCCCGAGCGTGTTTCCGCTGGCCCCGAGCAGCAAAAGCACCAGC   420
 T  V  S  S  C  S  T  K  G  P  S  V  F  P  L  A  P  S  S  K  S  T  S

GGTGGCACCGCAGCGCTGGGTTGCCTGGTGAAAGATTATTTCCCGGAACCGGTGACGGTGTCGTGGAACT   490
 G  G  T  A  A  L  G  C  L  V  K  D  Y  F  P  E  P  V  T  V  S  W  N

CAGGCGCCCTGACCAGCGGCGTGCACACCTTCCCGGCTGTCCTACAGTCCTCAGGACTCTACTCCCTCAG   560
 S  G  A  L  T  S  G  V  H  T  F  P  A  V  L  Q  S  S  G  L  Y  S  L  S

CAGCGTGGTGACCGTGCCCTCCAGCAGCTTGGGCACCCAGACCTACATCTGCAACGTGAATCACAAGCCC   630
 S  V  V  T  V  P  S  S  S  L  G  T  Q  T  Y  I  C  N  V  N  H  K  P

AGCAACACCAAGGTGGACAAGAAAGTTGAGCCCAAATCTTGTGACAAAACTCACACATGCCCACCGTGCC   700
 S  N  T  K  V  D  K  K  V  E  P  K  S  C  D  K  T  H  T  C  P  P  C

CAGCACCTGAACTCCTGGGGGGGACCGTCAGTCTTCCTCTTCCCCCCAAAACCCAAGGACACCCTCATGAT   770
 P  A  P  E  L  L  G  G  P  S  V  F  L  F  P  P  K  P  K  D  T  L  M  I

CTCCCGGACCCCTGAGGTCACATGCGTGGTGGTGGACGTGAGCCACGAAGACCCTGAGGTCAAGTTCAAC   840
 S  R  T  P  E  V  T  C  V  V  V  D  V  S  H  E  D  P  E  V  K  F  N

TGGTACGTGGACGGCGTGGAGGTGCATAATGCCAAGACAAAGCCGCGGGAGGAGCAGTACAACAGCACGT   910
 W  Y  V  D  G  V  E  V  H  N  A  K  T  K  P  R  E  E  Q  Y  N  S  T

ACCGGGTGGTCAGCGTCCTCACCGTCCTGCACCAGGACTGGCTGAATGGCAAGGAGTACAAGTGCAAGGT   980
 Y  R  V  V  S  V  L  T  V  L  H  Q  D  W  L  N  G  K  E  Y  K  C  K  V

CTCCAACAAAGCCCTCCCAGCCCCCATCGAGAAAACCATCTCCAAAGCCAAAGGGCAGCCCCGAGAACCA  1050
 S  N  K  A  L  P  A  P  I  E  K  T  I  S  K  A  K  G  Q  P  R  E  P

CAGGTGTACACCCTGCCCCCATCCCGGGATGAGCTGACCAAGAACCAGGTCAGCCTGACCTGCCTGGTCA  1120
 Q  V  Y  T  L  P  P  S  R  D  E  L  T  K  N  Q  V  S  L  T  C  L  V

AAGGCTTCTATCCCAGCGACATCGCCGTGGAGTGGGAGAGCAATGGGCAGCCGGAGAACAACTACAAGAC  1190
 K  G  F  Y  P  S  D  I  A  V  E  W  E  S  N  G  Q  P  E  N  N  Y  K  T

CACGCCTCCCGTGCTGGACTCCGACGGCTCCTTCTTCCTCTACAGCAAGCTCACCGTGGACAAGAGCAGG  1260
 T  P  P  V  L  D  S  D  G  S  F  F  L  Y  S  K  L  T  V  D  K  S  R

TGGCAGCAGGGGAACGTCTTCTCATGCTCCGTGATGCATGAGGCTCTGCACAACCACTACACGCAGAAGA  1330
 W  Q  Q  G  N  V  F  S  C  S  V  M  H  E  A  L  H  N  H  Y  T  Q  K

GCCTCTCCCTGTCTCCGGGTAAATGA                                              1356
 S  L  S  L  S  P  G  K  .
```

FIG. 18B

SEQUENCE LISTING

```
<160> NUMBER OF SEQ ID NOS: 4

<210> SEQ ID NO 1
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 1

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 2
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 2

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

-continued

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 3
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 3

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 451
<212> TYPE: PRT
<213> ORGANISM: Artificial Sequence
<220> FEATURE:
<223> OTHER INFORMATION: Synthetic Polypeptide
```

```
<400> SEQUENCE: 4

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Thr Leu Val Thr Val Ser Ser Cys Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
        435                 440                 445
Pro Gly Lys
    450
```

COMPOUNDS AND METHODS FOR THE TREATMENT OF TROP2 POSITIVE DISEASES

CROSS REFERENCE TO RELATED APPLICATIONS

This application claims priority under 35 U.S.C. § 119 to CN 201710687161.6, filed on Aug. 11, 2017, the contents of which are hereby expressly incorporated by reference in their entirety for all purposes and are assigned to the assignee hereof.

REFERENCE TO SEQUENCE LISTING SUBMITTED ELECTRONICALLY VIA EFS-WEB

The content of the electronically submitted sequence listing (Name: BioThera_013 Sequence Listing (4820-3059-3913 v1).txt; Size: 12,119 bytes; Date of Creation: Oct. 30, 2018) filed with this application is incorporated herein by reference in its entirety.

FIELD OF INVENTION

The present invention generally relates to compounds comprising antibodies, antigen-binding fragments thereof, polypeptides, and immunoconjugates that bind to TROP2 (TACSTD2). The present invention also relates to methods of using such TROP2-binding molecules for diagnosing and treating diseases, such as malignancies.

BACKGROUND OF INVENTION

Human trophoblast cell surface antigen 2 (Trop-2), a 40-kDa transmembrane glycoprotein encoded by the TACSTD2 gene (*Cytogenet Cell Genet.* 92:164-65 (2001)), was first identified in human trophoblast and choriocarcinoma cell lines (*Proc Natl Acad Sci USA.* 78:5147-50 (1981)). Its short intracytoplasmic tail plays a key role in controlling several pathways that regulate cellular functions such as cell-cell adhesion, cell proliferation, and mobility (*Oncogene.* 32:1594-600 (2013); *Dev Dyn.* 244:99-109 (2015)). Trop-2 protein expression is often increased in a variety of epithelial cancers (*J Histochem Cytochem.* 59:701-10 (2011); *Oncogene.* 32:222-33 (2013)). A role as a marker of human prostate cancer stem cells has been proposed for it, particularly in cancer initiation and progression (*Proc Natl Acad Sci USA.* 105:20882-87 (2008)). Trop-2 overexpression has been correlated with an aggressive malignant phenotype and poor prognosis (*PLoS ONE.* 9:e96993 (2014); *PLoS ONE.* 8:e75864 (2013); *Clin Cancer Res.* 12:3057-63 (2006). The data reviewed above have made it an attractive diagnostic and prognostic marker candidate. Trop-2 is also currently being tested as a therapeutic target, since an anti-Trop-2 antibody-drug conjugate is being used to treat patients with several metastatic neoplasms, including triple-negative breast cancer (TNBC) and non-small-cell and small-cell lung cancer (*Oncotarget* 6:22496-512 (2015)).

The clinical role of a new Trop-2-targeting ADC using the humanized RS7 antibody as a potentially improved treatment for TNBC (http://ClinicalTrials.gov number NCT01631552) has been proposed. This ADC, designated IMMU-132, used a moderately-toxic drug, SN-38, and thus the conjugation of drug to monoclonal antibody (mAb) has to be at a much higher ratio (~8:1) to achieve effectiveness. However, because the IMMU-132 ADC makes use of a moderately stable linker, the release half-life of SN-38 from IMMU-132 in human serum is about 24 h. Further, a rapid clearance of intact IMMU-132 was observed with a half-life of 11 h and mean residence time (MRT) of 15.4 h both in mice and in humans, which may result in a higher dosing frequency for clinical treatment. Despite IMMU-132 demonstrating encouraging efficacy on a variety of epithelial carcinomas, the incidence of neutropenia (the dose limited event) was shown to increase by up to 58%. Additionally, use of IMMU-132 was associated with severe diarrhea, which is common for topoisomerase inhibitors, such as SN-38. In contrast, Batansine-0808 utilizes a stable linker, which may have contributed to a longer MRT and lower dosing frequency. Thus, site-specific conjugate technology can not only improve the ADC homogeneity, but also result in better pharmacokinetics (PK) performance. Clearly, there is a need in the art to develop more efficacious and safer drugs against the Trop2 target.

Maytansinoids are highly cytotoxic compounds which inhibit the formation of microtubule protein polymerization (Remillard, et al., *Science* 189:1002-1005 (1975)). Maytansine was first isolated by Kupchan et al. (*J. Am. Chem. Sci* 94:1354-1356 (1972)) from the east African shrub *Maytenus serrata*. Maytansinoids including maytansinol and C-3 esters of maytansinol were also produced by certain microbes (U.S. Pat. No. 4,151,042). Various analogues of maytansinol with different cytotoxicity have also been prepared by synthetic chemistry (for review see *Chem. Pharm. Bull.* 52(1) 1-26 (2004)). Examples of maytansinoids include maytansine, mertansine (MD1), MD3 and MD4. Maytansine is a strong mitotic inhibitor and shows significant inhibitory activity against multiple tumors including Lewis lung carcinoma and B-16 melanocarcinoma solid murine tumor models. Maytansine was reported to inhibit the human acute lymphoblastic leukemia line C.E.M. at concentrations as low as $10^7$ g/mL (Wolpert-DeFillippes et al., *Biochem. Pharmacol.* 1735-1738 (1975)). It also showed to be 100- to 1000-fold more cytotoxic than conventional chemotherapeutic agents like methotrexate, daunorubicin, and vincristine (U.S. Pat. No. 3,896,111).

Ansamitocins, the bacterial maytansinoids, show an activity spectrum and effective dosage range similar to maytansine. They inhibit P388 leukemia at daily doses as low as 0.8 M1 g/kg. Ansamitocin P3 (AP3) was also shown to be effective against multiple cancer cell lines (for review see *Chem. Pharm. Bull.* 52(1):1-26 (2004)). The maytansinol C-3 esters with N-methyl-L-alanine derivatives are found to be much more cytotoxic than the corresponding esters of simple carboxylic acid and to be 100 times more cytotoxic than their epimers corresponding to N-methyl-D-alanine (U.S. Pat. Nos. 4,137,230; 4,260,608; Kawai, et al., *Chem. Pharm. Bull.* 32: 3441-3451 (1984); Widdison, et al., *J. Med. Chem.* 49:4392-4408 (2006)).

Maytansinoids were expected to have the capacity to treat many different cancers due to their highly toxic nature and the in vitro activities against multiple cancer cell lines. However, the toxicity also made this class of compounds unfavorable in human clinical trials as the side effects were intolerable for many patients (Issel et al., *Cancer Treat. Rev.* 5:199-207 (1978)). Accordingly, targeted delivery of cytotoxic compounds to cancer cells by conjugating toxic drugs to monoclonal antibodies (ADC for antibody drug conjugate) is proposed in order to reduce the side effects.

Antibody drug conjugates (ADCs) are composed of three key elements: antibody, linker, and drug. The selection of a particular antibody and drug will have a great impact on the efficacy and safety depending on the particular disease. Linker stability and the method by which the drug is conjugated to the antibody plays a critical role in the success or failure of the ADC drug development.

The efficacy of an ADC depends in part on combination of a variety of parameters, involving not only the specificity of the antibody and the potency of drugs, but also the linker's stability or sensitivity to cleavage, the cell surface triggered the internalization, trafficking, and subsequent release of the active cytotoxic payload. Thus, ADC comprising different drug linkers or with different antibodies against the same target can vary significantly in their utility.

SUMMARY OF THE INVENTION

In one aspect, provided herein is an anti-TROP2 antibody that is conjugated with maytansinoid molecules, thus targeting diseased cells or tissues. The anti-TROP2 antibody binds to an antigen in the diseased cells or tissues. A drug conjugated to the antibody exerts a cytotoxic, cytostatic, or immunosuppressive effect on the antigen-expressing cells to treat or prevent recurrence of TROP2-positive cancers. The high affinity of the antibody drug conjugate ensures that the cytotoxic maytansinoid targets the tumor cells. Otherwise, the highly toxic maytansinoid will become systemically bound to unintended targets which results in very high and often unacceptable toxicity. The present technology provides a method to treat cancers by exerting cellular inhibitory or killing effect of maytansinoid on the TROP2 positive cells, while minimizing the undesirable side effects of maytansinoid, such as bystander killing effects on antigen negative cells.

In another aspect, provided herein is an anti-TROP2 antibody conjugated with a maytansinoid compound, wherein the maytansinoid compound is linked to an anti-TROP2 antibody via a linker that is not acid labile, not peptidase cathepsin sensitive, and does not contain a disulfide bond and provides stability during circulation while being able to release the drug once inside the cells. Such linkers are contemplated to provide stability to the conjugated molecule prior to endocytosis, such as during circulation, to prevent premature degradation of the linker and release of the toxic drug, thus minimize the toxic effect of the drug. In some embodiments, the maytansinoid-linker portion of the conjugate is N2'-deacetyl-N2'-(6-maleimido-1-oxo-hexyl)-maytansine (3AA-MDC or batansine), or a derivative thereof. In some embodiments, the conjugate has a drug load of at least one drug molecule per antibody for improved safety and activity. Surprisingly, the antibody remain sufficiently stable for targeted delivery of the drug to target cells despite the high drug load.

In some embodiments, provided herein is a maytansinoid linker anti-TROP2 antibody conjugate of Formula Ia or Ib:

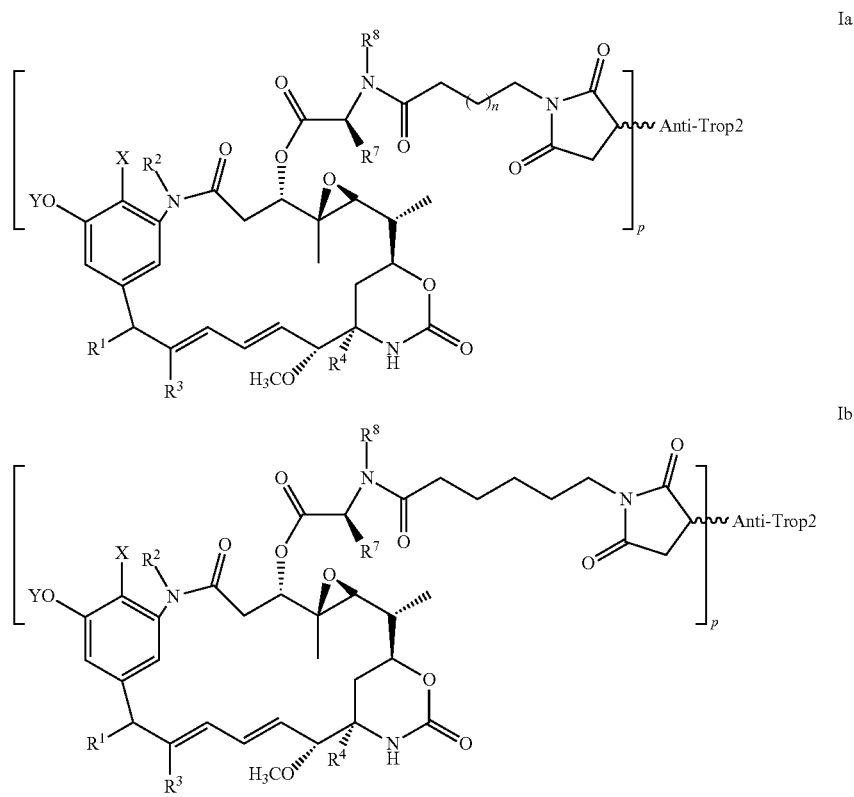

or a pharmaceutically acceptable salt or solvate thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_1$-$C_6$ alkyl;

n is 0, 1, 2, 3, 4, 5, 6, 7 or 8;

p is selected from 1, 2, 3, 4, 5, 6, 7, 8, 9, 10; and

Anti-TROP2 is an anti-TROP2 antibody.

In another aspect, provided herein is a composition comprising the above-described maytansinoid linked anti-TROP2 antibody conjugate, such as a compound of Formula Ia.

In another aspect, provided herein is a method of preparing the above-described maytansinoid linked anti-TROP2 antibody conjugate which method comprises contacting an anti-TROP2 antibody with one or more maytansinoid compounds described herein capable of being conjugated to the anti-TROP2 antibody.

In another aspect, provided herein is a method for targeting a maytansinoid to TROP2 antigen positive cells or tissues with an anti-TROP2 antibody conjugated with maytansinoids described herein.

In some embodiments, the anti-TROP2 antibody provided by the present invention may be BAT0806, which comprises an amino acid sequence of the anti-Trop2 light chain shown in SEQ ID NO:1, and the anti-TROP2 heavy chain shown in SEQ ID NO:2, wherein the anti-TROP2 antibody or TROP2 antigen binding unit is expressed through an expression vector by CHO-BAT. The host cell line was derived from Chinese hamster ovary cell line CHO-K1 (ATCC #CCL-61), and was adapted to suspension growth. In some embodiments, the anti-Trop2 antibody provided by the present invention may be BAT0807, which comprises an amino acid sequence of the anti-TROP2 light chain shown in SEQ ID NO:3, and the anti-TROP2 heavy chain shown in SEQ ID NO:4, wherein the anti-TROP2 antibody or TROP2 antigen binding unit is expressed through a expression vector by CHO-BAT. The host cell line was derived from Chinese hamster ovary cell line CHO-K1(ATCC #CCL-61), and was adapted to suspension growth. In other embodiments, the anti-TROP2 antibody provided by the present invention may be BAT0808, which comprises an amino acid sequence of the anti-Trop2 light chain shown in SEQ ID NO:3, and the anti-TROP2 heavy chain shown in SEQ ID NO:4, wherein the anti-TROP2 antibody or TROP2 antigen binding unit is expressed by a expression vector by CHO-BAT-KF. The host cell line was knocked out the α-(1,6)-fucosyltransferase, which was characterized by the expressed antibody has a fucose content of 0-5% and an ADCC-enhanced effect. The host cell was deposited at the China Type Culture Collection, Wuhan University, Wuhan, Hubei, Province, China, on Aug. 10, 2017 with Accession No.: CCTCC NO: C2017127. In some embodiments, the anti-TROP2 antibody provided by the present invention may be other TROP2 antigen binding units.

In another aspect, provided herein is a method for treatment of proliferative disorders such as tumors, inflammatory or immunologic diseases such as graft rejections, and other diseases that can be treated by targeted therapy in a subject in need of the treatment, wherein the disease is characterized by cells comprising an antigen that binds to an anti-TROP2 antibody, said method comprising administering to the subject an effective amount of the anti-TROP2 antibody drug conjugate described herein.

BRIEF DESCRIPTION OF THE DRAWINGS

FIGS. 17A and 17B show the light chain and heavy chain amino acid sequences of anti-TROP2 antibody BAT0806.

FIGS. 18A and 18B show the light chain and heavy chain amino acid sequences of anti-TROP2 antibody BAT0807 and BAT0808.

DETAILED DESCRIPTION OF THE INVENTION

Definitions

Figure 1A:
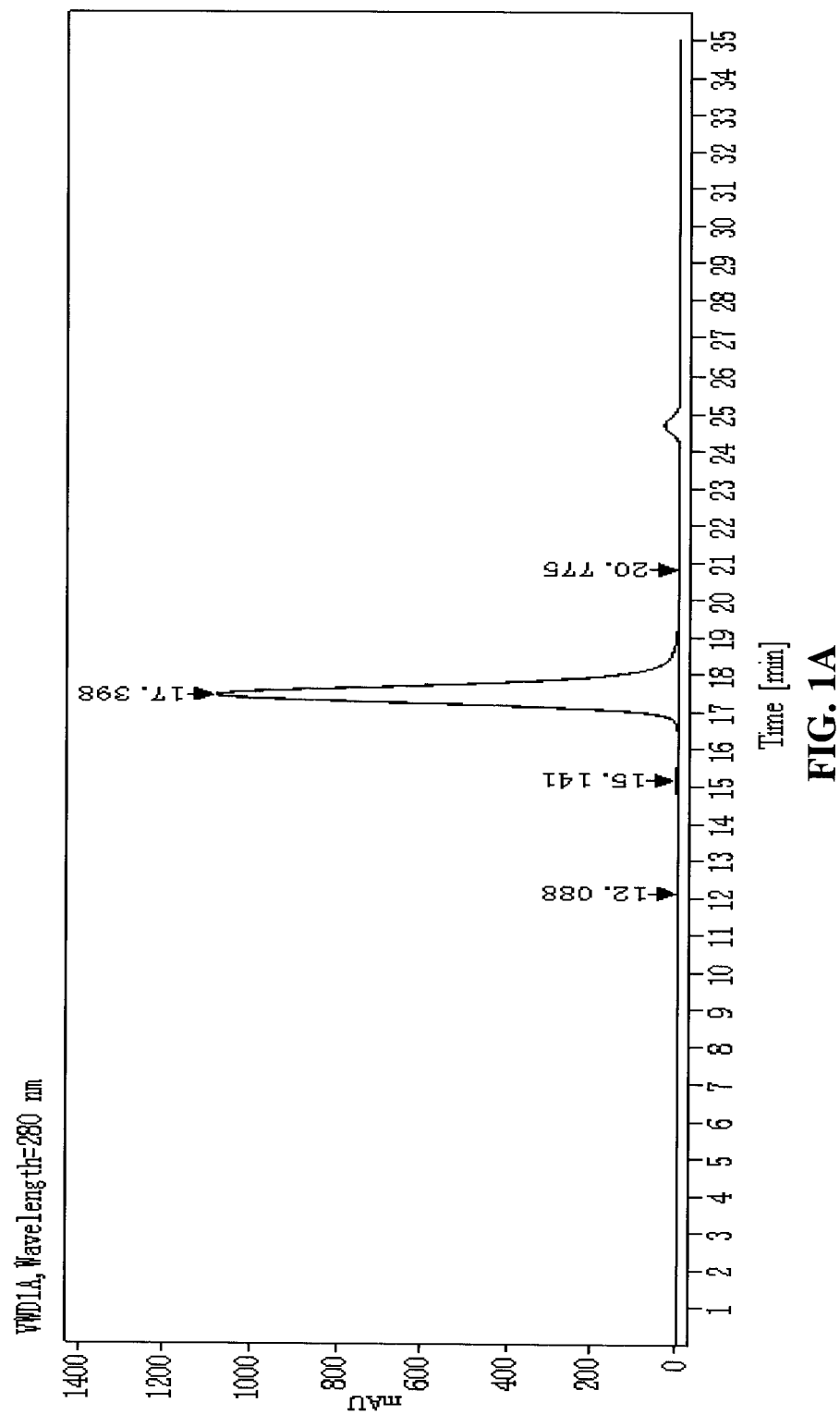
FIGS. 1A and 1B show measuring the aggregation rate of BAT0806 and Batanine-0806 through the dimensional exclusion chromatography.
Figure 1B:
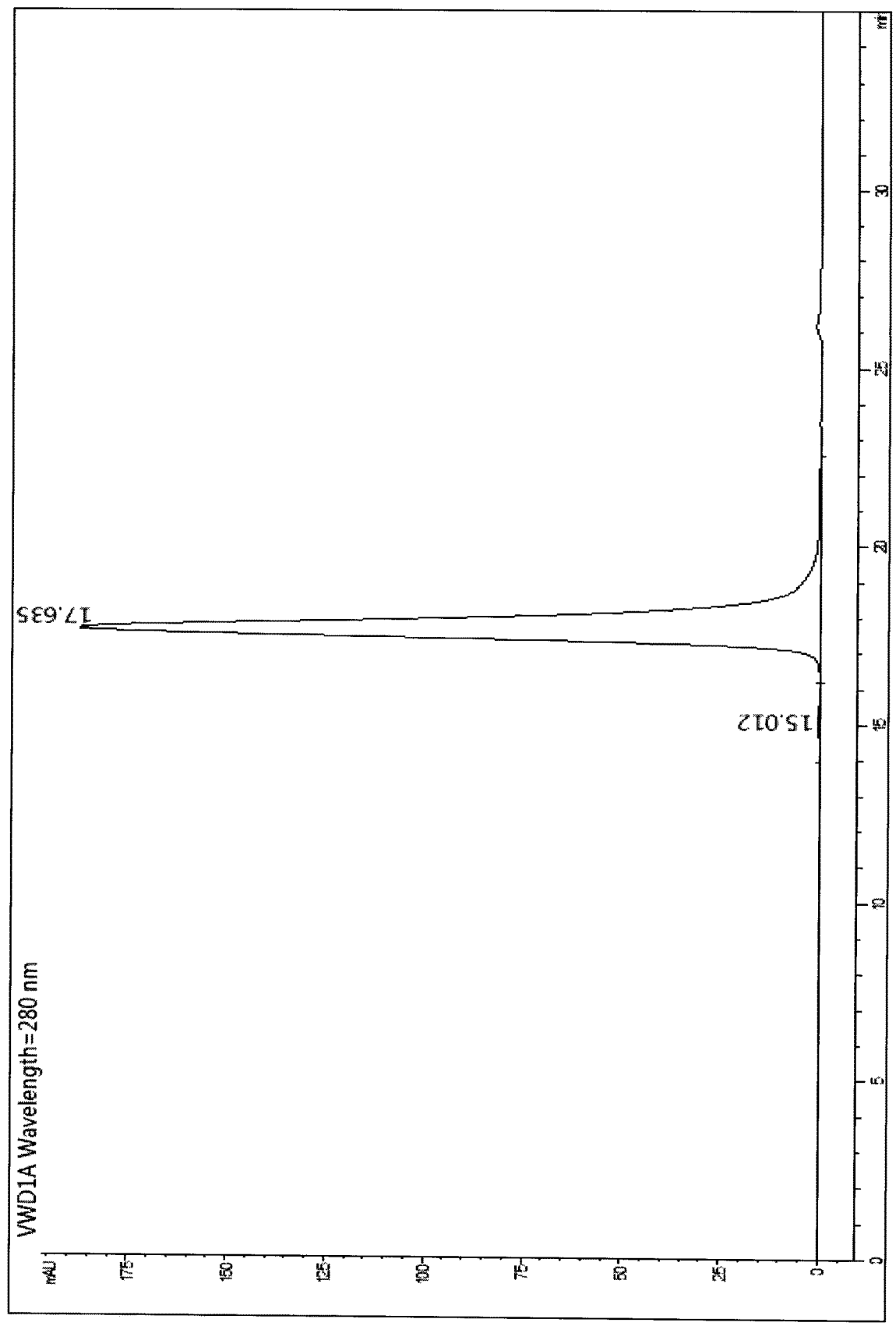
Figure 2A:
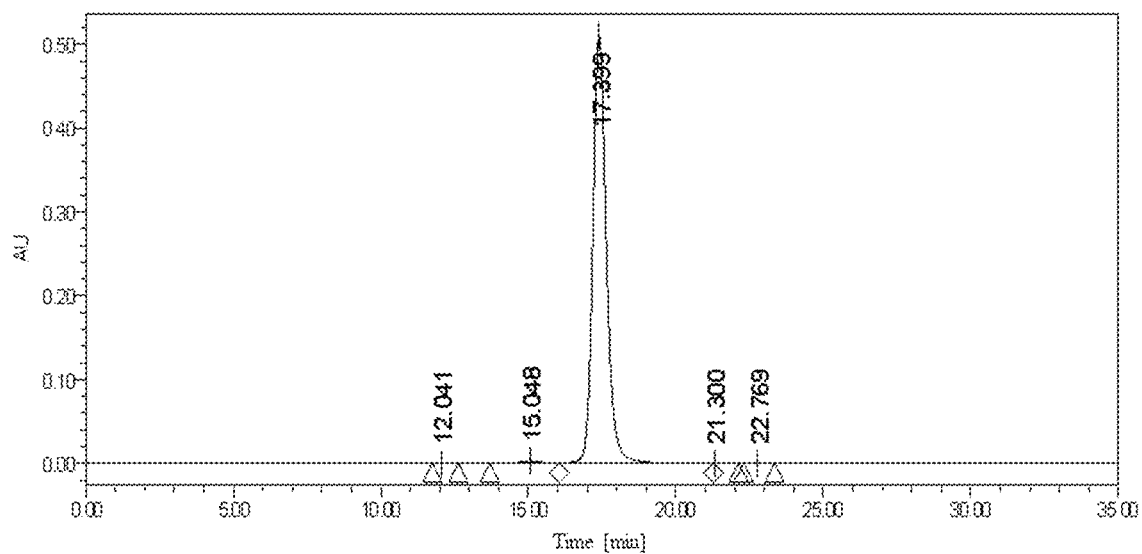
FIGS. 2A and 2B show measuring the aggregation rate of BAT0808 and Batanine-0808 through the dimensional exclusion chromatography.
Figure 2B:
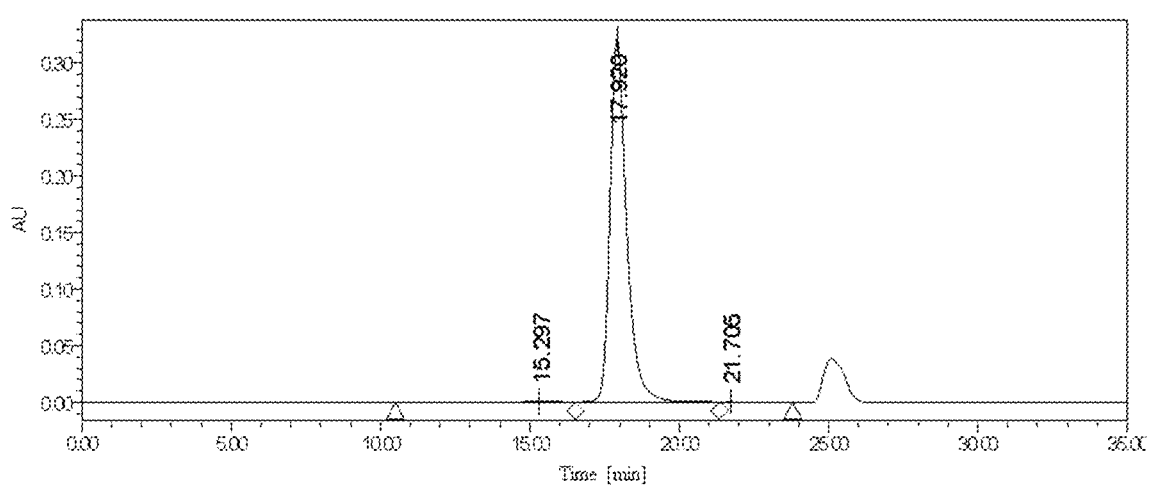
Figure 3:
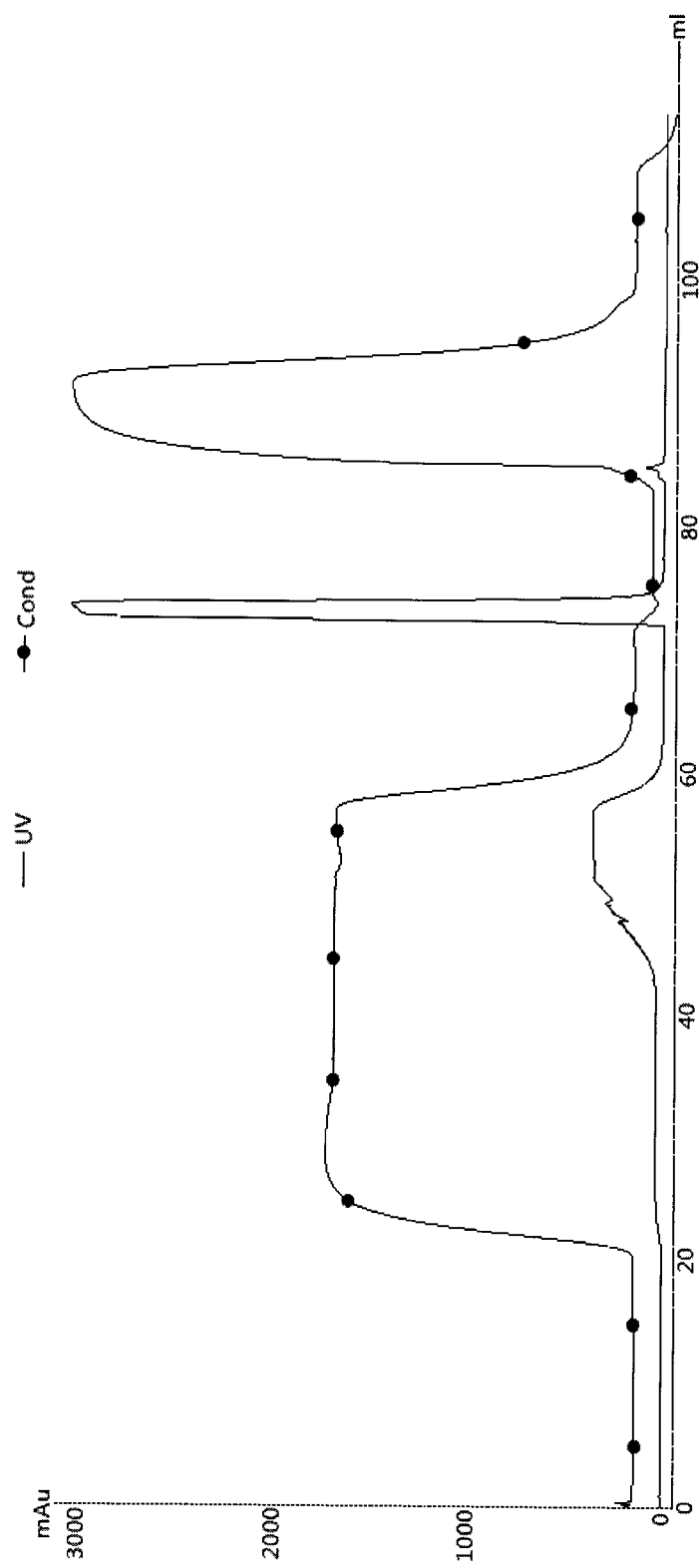
FIG. 3 shows the map of the Sephadex G25 (M) column separating the antibody drug conjugate Batansine-0806.
Figure 4:
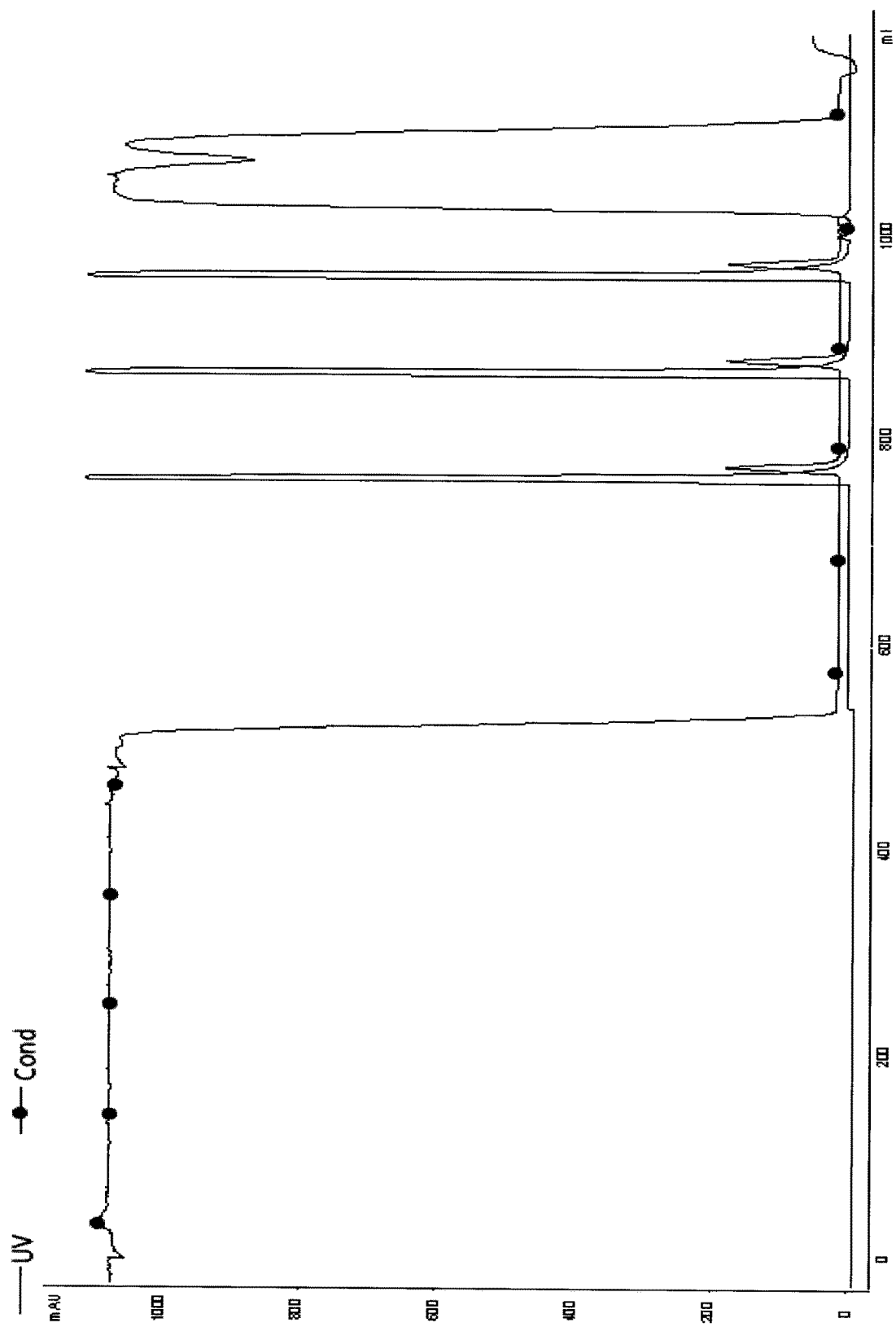
FIG. 4 shows the map of the Sephadex G25 (M) column separating the antibody drug conjugate BAT0806-CL2A-SN-38.
Figure 5:
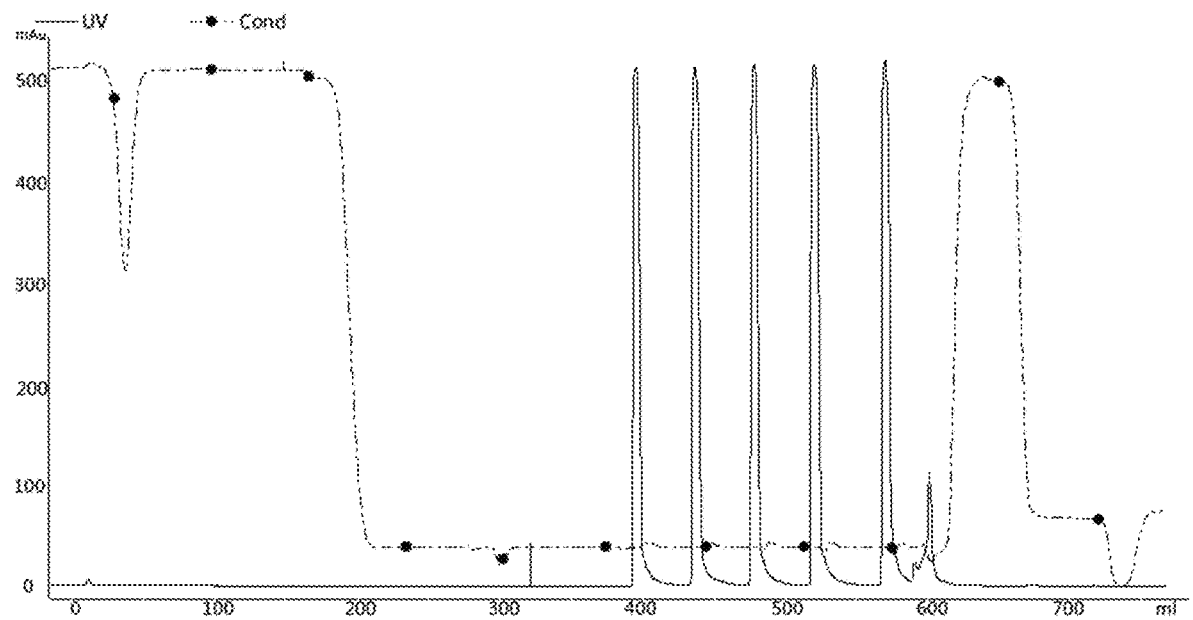
FIG. 5 shows the map of the Sephadex G25 (M) column separating the antibody drug conjugate Batansine-0808.
Figure 6:
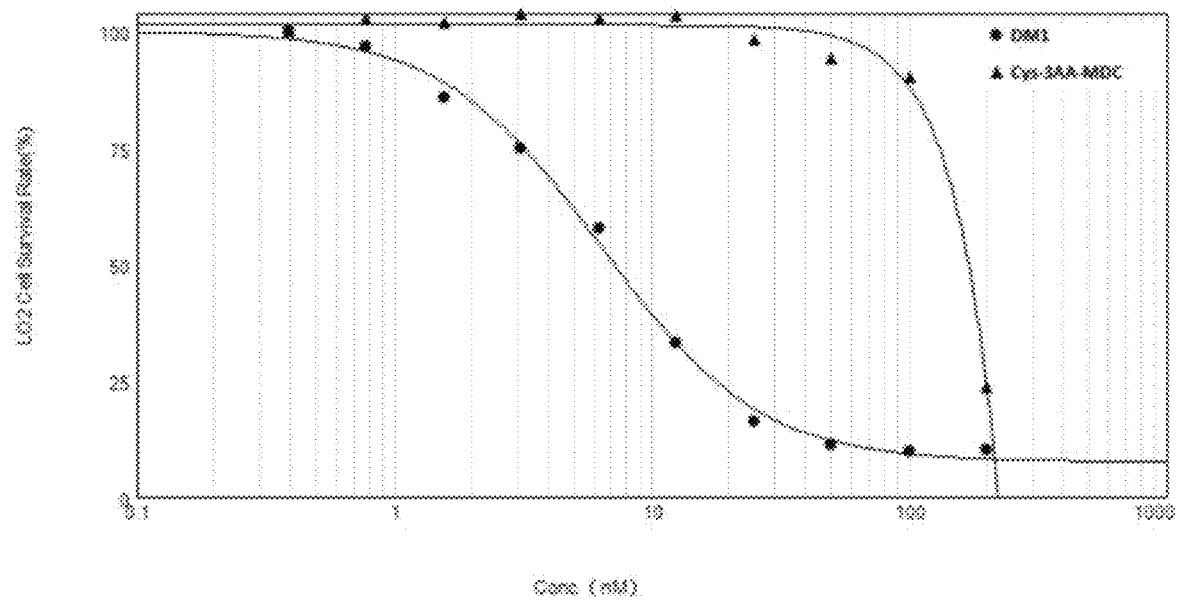
FIG. 6 shows the Proliferation Inhibitory effect of DM1 and Cys-3AA-MDC towards LO2 cells.

As used herein, the following definitions shall apply unless otherwise indicated.

As used herein, unless otherwise stated, the singular forms "a," "an," and "the" include plural reference. Thus, for example, a reference to "a compound" includes a plurality of compounds.

As used herein, "about" will be understood by persons of ordinary skill in the art and will vary to some extent depending upon the context in which it is used. If there are uses of the term which are not clear to persons of ordinary skill in the art, given the context in which it is used, "about"

will mean up to plus or minus 10% or plus or minus 5%, or plus or minus 1% of the particular term.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, "maytansinoid" refers to a maytansine analogue, including stereoisomers thereof. Maytansine can be isolated from plants of the genus *Maytenus* U.S. Pat. No. 3,896,111). It is of the formula:

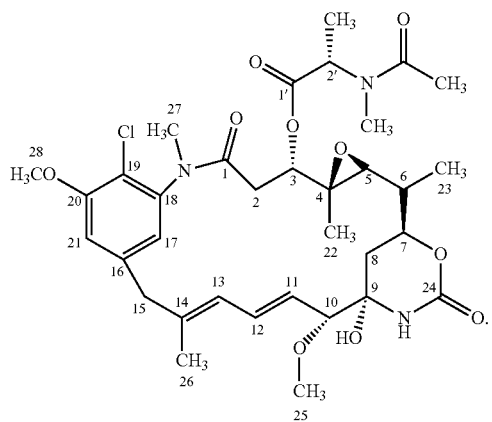

Maytansinoids are compounds having the ring structure of maytansine with one or more modifications of the substituents on the ring.

"Alkyl" refers to monovalent saturated aliphatic hydrocarbyl groups having from 1 to 10 carbon atoms and preferably 1 to 6 carbon atoms. $C_v$ alkyl wherein v is an integer represents an alkyl having v carbons. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). "Alkylene" is a divalent saturated aliphatic hydrocarbyl groups having from 1 to 10 carbon atoms and preferably 1 to 6 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' and R" is hydrogen but not both. When referring to a disubstituted amino, it is meant that neither R' and R" are hydrogen.

"Amino acid" refers any compound, whether natural, unnatural or synthetic, which includes both an amino group and a carboxy group. Examples of amino acid include, but are not limited to glycine (NH$_2$CH$_2$COOH), cysteine, alanine, N-methyl-L-alanine, including both the D and L optical isomers. "Amino acid side chain" refers to the substituent that replaces a hydrogen of the methylene group of glycine or glycine derivatives, such as N-alkylglycine or glycine esters. Examples of an amino acid side chain include, but are not limited to the side chains of the natural amino acids, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or CO$_2$H or salts thereof.

"Carboxylic acid" refers to a compound having at least one carboxy.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5] dec-8-yl:

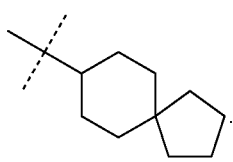

Cycloalkylene refers to a cyclic alkylene.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 6 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or partially saturated, but not aromatic, group having from 3 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Substituted alkyl," "substituted alkenyl," "substituted alkynyl," "substituted cycloalkyl," "substituted cycloalkenyl," "substituted aryl," "substituted heteroaryl" or "substituted heterocyclic" refers to alkyl, alkenyl, alkynyl, cycloalkyl, cycloalkenyl, aryl, heteroaryl or heterocyclic groups, respectively, which are substituted with 1 to 5, preferably 1 to 3, or more preferably 1 to 2 substituents selected from the group consisting of alkyl, halo alkyl, —O—$R^{20}$, —S—$R^{20}$, alkenyl, alkynyl, —C(=O)$R^{20}$, —C(=S)$R^{20}$, —C(=O)O$R^{20}$, —$NR^{20}$C(=O)$R^{21}$, —OC(=O)$R^{21}$, —$NR^{20}R^{20}$, —C(=O)$NR^{20}R^{20}$, —C(=S)$NR^{20}R^{20}$, —$NR^{20}$C(=O)$NR^{20}R^{20}$, —$NR^{20}$C(=S)$NR^{20}R^{20}$, —OC(=O)$NR^{20}R^{20}$, —$SO_2NR^{20}R^{20}$, —$OSO_2NR^{20}R^{20}$, —$NR^{20}SO_2NR^{20}R^{20}$, —C(=$NR^{20}$)$NR^{20}R^{20}$, aryl, —$NR^{20}$C(=O)$OR^{21}$, —OC(=O)$OR^{21}$, cyano, cycloalkyl, cycloalkenyl, —$NR^{20}$C(=$NR^{20}$)$NR^{20}R^{20}$, halo, hydroxy, heteroaryl, heterocyclic, nitro, —$SO_3H$, —$SO_2R^{21}$, and —$OSO_2R^{21}$, wherein each $R^{20}$ is selected from the group consisting of hydrogen, alkyl, alkenyl, alkynyl, aryl, cycloalkyl, cycloalkenyl, heteroaryl, and heterocyclic or two $R^{20}$ with the atom(s) bound thereto form a heterocyclic ring, and $R^{21}$ is selected from the group consisting of alkyl, alkenyl, alkynyl, aryl, cycloalkyl, cycloalkenyl, heteroaryl, and heterocyclic.

"Nitro" refers to the group —$NO_2$.

"Oxo" refers to the atom (=O) or (—O—).

"Spiro ring systems" refers to bicyclic ring systems that have a single ring carbon atom common to both rings.

"Thiol" refers to the group —SH.

"Thiocarbonyl" refers to the divalent group —C(S)— which is equivalent to —C(=S)—.

"Thione" refers to the atom (=S).

"Compound" or "compounds" as used herein is meant to include the stereoiosmers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Solvate" refer to an association of a solvent with a compound, in the crystalline form. The solvent association is typically due to use of the solvent in the synthesis, crystallization, and/or recrystallization of the compound. "Solvate" includes hydrate which is an association of water with a compound, in the crystalline form.

"Patient" or "subject" refers to mammals and includes humans and non-human mammals. In some embodiments, the term refers to humans. In some embodiments, the term refers to non-human mammals, such as wild, domestic, and farm animals. In yet other embodiments, the term refers to dogs, cats, mice, rats, rabbits, guinea pigs, or primates such as chimpanzees.

"Pharmaceutically acceptable salt" refers to pharmaceutically acceptable salts of a compound, which salts are derived from a variety of organic and inorganic counter ions well known in the art and include, by way of example only, when the molecule contains an acidic functionality, salts of organic or inorganic bases, such as sodium, potassium, calcium, magnesium, ammonium, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and tetraalkylammonium, and the like; and when the molecule contains a basic functionality, salts of organic or inorganic acids, such as hydrochloride, hydrobromide, tartrate, mesylate, acetate, maleate, and oxalate. Other non-limiting examples of acids include sulfuric acid, nitric acid, phosphoric acid, propionic acid, glycolic acid, pyruvic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

"Effective amount" is intended to mean an amount of an active compound or pharmaceutical agent that elicits the biological or medicinal response in a tissue, system, animal, individual or human that is being sought by a researcher, veterinarian, medical doctor or other clinician, which includes treating a disease.

"Administering" a composition may be accomplished by oral administration, injection, infusion, parenteral, intravenous, mucosal, sublingual, intramuscular, intradermal, intranasal, intraperitoneal, intraarterial, subcutaneous absorption or by any method in combination with other known techniques. In one embodiment of the invention, administration occurs systemically.

As used herein, the phrase "in need thereof" means that the subject has been identified as having a need for the particular method or treatment. In some embodiments, the identification can be by any means of diagnosis. In any of the methods and treatments described herein, the subject can be in need thereof.

Anti-TROP2 Antibody Drug Conjugates

In one aspect, disclosed herein is a maytansinoid conjugated to an anti-TROP2 antibody via a linker that is not acid labile, not peptidase cathepsin sensitive, and that is stable in circulation while being able to release the cytotoxic drug inside the cells. In another aspect, disclosed herein is an antibody drug conjugate in which the drug is specifically linked at an artificial cysteine site located on the heavy chain of the antibody, and the antibody drug conjugate has an average drug load of 2.0 molecules per antibody.

Maytansinoids suitable for attaching the linking group include maytansinol and maytansinol analogues which can be isolated from natural sources according to known methods, produced using biotechnologies (see e.g., Yu et al., PNAS 99:7968-7973 (2002)), or prepared synthetically according to known methods (see e.g., Cassady et al., Chem. Pharm. Bull. 52(1):1-26 (2004)).

Certain examples of suitable maytansinol analogues include:
(1) C-19-dechloro (U.S. Pat. No. 4,256,746) (prepared by LAH reduction of ansamytocin P2);
(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using lithium aluminium hydride (LAH));
(3) C-20-demethoxy, C-20-acyloxy (—OCOR), +/−dechloro (U.S. Pat. No. 4,294,757) (prepared by acylation using acyl chlorides);
(4) C-9-SH (U.S. Pat. No. 4,424,219) (prepared by the reaction of maytansinol with $H_2S$ or P2S5);
(5) C-14-hydroxymethyl ($CH_2OH$) or acyloxymethyl ($CH_2OC(=O)$phenyl or $CH_2OC(=O)(C_1$-$C_5$ alkyl)) (U.S. Pat. No. 4,331,598) (prepared from *Nocardia*);
(6) C-15-hydroxy/acyloxy (U.S. Pat. No. 4,364,866) (prepared by the conversion of maytansinol by *Streptomyces*);
(7) C-15-methoxy (U.S. Pat. Nos. 4,313,946 and 4,315,929) (isolated from Trewia nudlflora);
(8) C-18-N-demethyl (U.S. Pat. Nos. 4,362,663 and 4,322,348) (prepared by the demethylation of maytansinol by *Streptomyces*); and
(9) 4,5-deoxy (U.S. Pat. No. 4,371,533) (prepared by the titanium trichloride/LAH reduction of maytansinol).

Many positions on maytansinol can be useful as the linkage position, depending upon the type of linker used. For example, for forming an ester linkage, the C-3 position having a hydroxyl group, the C-14 position modified with hydroxymethyl, the C-15 position modified with a hydroxyl group and the C-20 position having a hydroxyl group are all suitable. In some embodiments, the linkage position is the C-3 position.

In some embodiments, provided is a compound of Ia or Ib

Ia

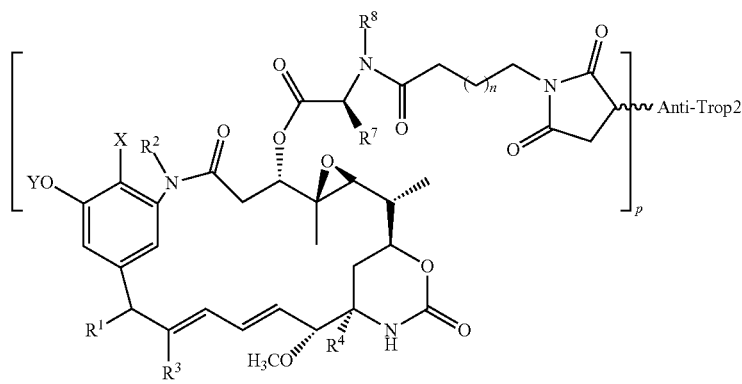

-continued

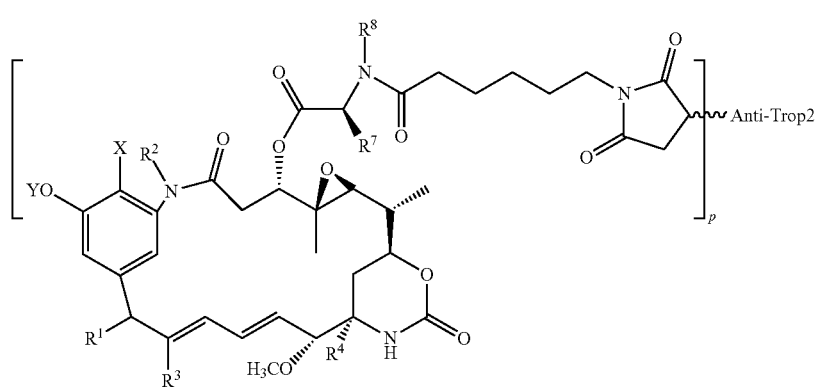

Ib or a pharmaceutically acceptable salt or solvate thereof, wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_1$-$C_6$ alkyl;
n is 0, 1, 2, 3, 4, 5, 6, 7 or 8;
p is selected from 1, 2, 3, 4, 5, 6, 7, 8, 9, 10; and
Anti-TROP2 is an anti-TROP2 antibody.
In some embodiments, the compound of Ia is anti-TROP2 antibody or the maytansinoid linker anti-TROP2 antibody conjugates can be substituted by other suitable cytotoxic agents, for example, an auristatin, a DNA minor groove binding agent, a DNA minor groove alkylating agent, an enediyne, a lexitropsin, a duocarmycin, a taxane, a puromycin, a dolastatin, and a vinca alkaloid. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In some embodiments, the cytotoxic agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-3, DM-4, or eleutherobin. Suitable immunosuppressive agents include, for example, gancyclovir, etanercept, cyclosporine, tacrolimus, rapamycin, cyclophosphamide, azathioprine,

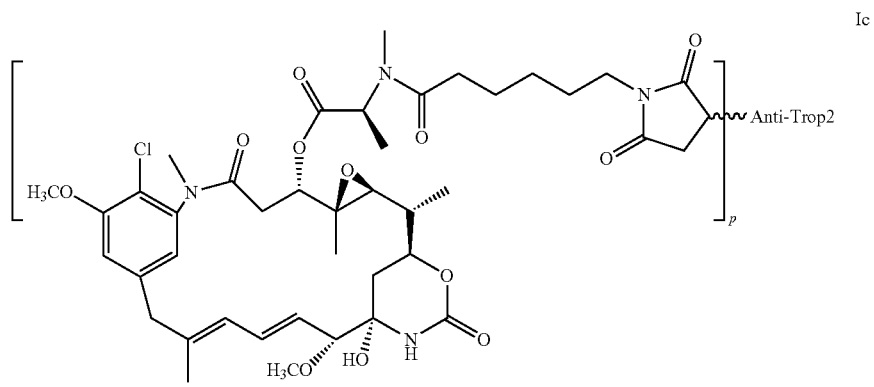

Ic or a pharmaceutically acceptable salt or solvate thereof, wherein Anti-TACSTD2 is an anti-TROP2 (TACSTD2) antibody.

In some embodiments, the anti-Trop2 antibody is expressed through a expression vector by CHO-BAT-KF (Accession No.: CCTCC NO: C2017127). The cell line was knocked out α-(1,6)-fucosyltransferase, characterized by enhanced ADCC function. These antibodies include but are not limited to the BAT0806, BAT0807, BAT0808 or other antigen-binding fragments already described.

The maytansinoid component of the maytansinoid derivatives having a linking group capable of conjugating to an mycophenolate mofetil, methotrexate, cortisol, aldosterone, dexamethasone, a cyclooxygenase inhibitor, a 5-lipoxygenase inhibitor, or a leukotriene receptor antagonist. In some embodiments, the cytotoxic agent is pyrrolobenzodiazepine (PBD) or its dimer, AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, DM-3, DM-4, or netropsin.

The maytansinoid component of the maytansinoid derivatives having a linking group capable of conjugating to an anti-TROP2 antibody and the maytansinoid linker anti-TROP2 antibody conjugates can also be substituted by a suitable immunosuppressive agent, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

Anti-TROP2 Antibody

Anti-TROP2 antibody include fragments of antibodies (polyclonal and monoclonal) such as Fab, Fab', F(ab')$_2$, and Fv (see, e.g., Parham, *J. Immunol.* 131:2895-2902 (1983); Spring et al., *J. Immunol.* 113:470-478 (1974); Nisonoff et al., *Arch. Biochem. Biophys.* 89:230-244 (1960)); domain antibodies (dAbs) and antigen-binding fragments thereof, including camelid antibodies (see, e.g., Desmyter et al., *Nature Struct. Biol,* 3:752 (1996)); shark antibodies called new antigen receptors (IgNAR) (see, e.g., Greenberg et al., *Nature,* 374:168 (1995); Stanfield et al. *Science* 305:1770-1773 (2004)), and antibody with engineered glycan profiles for increased ADCC activity, and in some cases, antibodies with engineered amino acid(s) for site-specific toxin conjugation.

Monoclonal antibody techniques allow for the production of anti-TROP2 antibody in the form of specific monoclonal antibodies. Particularly well known in the art are techniques for creating monoclonal antibodies produced by immunizing mice, rabbits, or any other mammal with the antigen of interest such as the tumor specific antigens isolated from the target cell. Another method of creating anti-TROP2 antibody is using phage libraries of scFv (single chain variable region), specifically human scFv (see, e.g., Griffiths et al., U.S. Pat. Nos. 5,885,793 and 5,969,108; McCafferty et al., WO 92/01047; Liming et al., WO 99/06587), or domain antibodies using yeast selection system (see, e.g., U.S. Pat. No. 7,195,595). In addition, resurfaced antibodies such as those disclosed in U.S. Pat. No. 5,639,641 may also be used, as may chimerized or humanized antibodies.

The antibody moiety may be a monoclonal antibody, an antigen-binding antibody fragment, a bispecific or other multivalent antibody, or other antibody-based molecule. The antibody can be of various isotypes, preferably human IgG1, IgG2, IgG3 or IgG4, more preferably comprising human IgG1 hinge and constant region sequences. The antibody or fragment thereof can be a chimeric, a humanized, or a human antibody, as well as variations thereof, such as half-IgG4 antibodies (referred to as "unibodies"), as described by van der Neut Kolfschoten et al. *Science* 317: 1554-1557 (2007). More preferably, the antibody or fragment thereof may be designed or selected to comprise human constant region sequences that belong to specific allotypes, which may result in reduced immunogenicity when the ADC is administered to a human subject. Preferred allotypes for administration include a non-G1 ml allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

Selection of a particular anti-TROP2 antibody is a matter of choice that depends upon the disease type, cells and tissues that are to be targeted.

In some embodiments, the anti-TROP2 antibody is fully human monoclonal antibody, and in other embodiments, the anti-TROP2 antibody is humanized monoclonal antibody.

Anti-TROP2 antibodies that have specificity to a tumor antigen can be used. A "tumor antigen" as used herein, refers to an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

Anti-TROP2 antibody shows high affinity specific to TROP2 which is highly expressed in a range of solid tumors including the breast cancer, cervical cancer, colorectal cancer, esophageal cancer, gastric cancer, lung cancer, oral squamous cell carcinoma, ovarian cancer, prostate cancer, pancreatic cancer, thyroid cancer, urinary bladder cancer, ovarian cancer, glioma, porta hepatis bile duct cancer, kidney cancer, colorectal cancer, T cell lymphoma, glioblastoma, medulloblastoma, Urothelial Carcinoma, head and neck cancer and Kaposi's sarcoma and so on, but rarely or even not expressed in normal tissue cells.

Trop-2 is a type-I transmembrane protein that has been cloned from both human (Fornaro et al., *Int J Cancer* 62:610-8 (1995)) and mouse cells (Sewedy et al., *Int J Cancer* 75:324-30 (1998)). In addition to its role as a tumor-associated calcium signal transducer (Ripani et al., *Int J Cancer* 76:671-6 (1998)), the expression of human Trop-2 was shown to be necessary for tumorigenesis and invasiveness of colon cancer cells, which could be effectively reduced by administering a polyclonal antibody against the extracellular domain of Trop-2 (Wang et al., *Mol Cancer Ther* 7:280-5 (2008)).

Trop-2 as a therapeutic target for solid cancers has garnered growing interest (Cubas et al., *Biochim Biophys Acta* 1796:309-14 (2009)) because of reports of the protein being overexpressed in breast (Huang et al., *Clin Cancer Res* 11:4357-64 (2005)), colorectal (Ohmachi et al., *Clin Cancer Res* 12:3057-63 (2006); Fang et al., *Int J Colorectal Dis* 24:875-84 (2009)), and oral squamous cell (Fong et al., *Modern Pathol* 21:186-91 (2008)) carcinomas. The latest evidence that prostate basal cells expressing high levels of Trop-2 are enriched for in vitro and in vivo stem-like activity is particularly noteworthy (Goldstein et al., *Proc Nat Acad Sci USA* 105:20882-7 (2008)).

For example, flow cytometry and immunohistochemical staining studies have shown that the RS7 Mab, an anti-trop monoclonal antibody, detects antigen on a variety of tumor types, with limited binding to normal human tissue (Stein et al., (1990)). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., (1990); Stein et al., (1991)).

Strong RS7 staining has been demonstrated in tumors from the lung, breast, bladder, ovary, uterus, stomach, and prostate. (Stein et al., *Int. J. Cancer* 55:938 (1993)) The lung cancer cases comprised both squamous cell carcinomas and adenocarcinomas. (Stein et al., *Int. J. Cancer* 55:938 (1993)). Both cell types stained strongly, indicating that the RS7 antibody does not distinguish between histologic classes of non-small-cell carcinoma of the lung.

It is contemplated that anti-TROP2 antibody can be modified to introduce an amino acid sequence having improved antibody-dependent cellular cytotoxicity (ADCC). For instance, amino acids in the Fc and/or hinge region can be modified to achieve improved ADCC. Examples of IgG1-Fc that mediates improved ADCC, as well as methods of screening for such sequences, are known in the art (e.g., Stewart et al. *Protein Eng Des Sel.* 24(9): 671-8 (2011)). Antibodies can also be engineered with reduced or no fucose that results in increased Fc-gamma III affinity, and thus increased ADCC activity.

Conjugation of a Drug to an Anti-TROP2 Antibody

As discussed, a drug (e.g., a maytansinoid drug derivative) can be conjugated to an anti-TROP2 antibody through a linker. In one embodiment, the anti-TROP2 antibody can be modified with an appropriate bifunctional modifying agent. In some embodiments, a group comprising a thiol (SH) group (also referred to as thio-comprising group) can be introduced to the side-chain of an amino acid residue, such as the side-chain of a lysine, on the anti-TROP2 antibody. For example, the amino group of a lysine residue on the anti-TROP2 antibody can be converted to a thiol-comprising group by reaction with 2-iminothiolane (Traut's Reagent), or with N-succinimidyl 3-(2-pyridyldithio)propanoate (SPDP), N-succinimidyl 4-(2-pyridyldithio)butanoate (SPDB), etc. and followed by reduction with a reducing reagent, such as 2-mercaptoethanol, dithiothreitol (DTT) or tris(2-carboxyethyl)phosphine (TCEP). In some embodiments, to allow proper coupling, the anti-TROP2 antibody can be engineered with a cysteine, via mutagenesis, or inserted in a specific location that results minimal effect on the antibody activities including affinity, specificity, ADCC, CDC, ADCP, and immunogenicity. For example, the engineered cysteine residue may be inserted at the positions of heavy chain 114 and/or 239 and/or light chain 149 and/or 205 of the TROP2 antibody, and can be used to conjugate toxin to the antibody on specific sites. Multiple cysteines can be engineered to the anti-TROP2 antibody molecule.

Non-limiting examples of thiol-comprising group that can replace the side-chain amino group of a lysine residue include —NHC(=NH)(CH$_2$)$_n$SH and —NHC(O)(CH$_2$)$_n$SH, wherein n is 1, 2, 3, 4, 5 or 6. When a thiol-comprising group is introduced to an amino acid residue, the amino acid residue is referred to as thiolated amino acid. For example, when the side-chain amino group of a lysine residue is converted to a thio-comprising group, the lysine residue is referred to as thiolated lysine. The number of free thiol (SH) group introduced in an anti-TROP2 antibody may vary, such as between 1 and about 20, or 1 to 10, and or 1 to 5. The linkers or drug-linkers can form bonds with the free thiol (SH) group of a cysteine residue or a thiolated lysine residue on the anti-TROP2 antibody. In some embodiments, the number of linkers or drug-linkers that form bonds with cysteine residues in the anti-TROP2 antibody is between 1 and about 10. In some embodiments, the number of such formed bonds is at least 1, or alternatively at least 2, or 3, or 4, or 5. In some embodiments, the number of such formed bonds is no more than 10, or alternatively no more than 9, or 8, 7, 6, 5, or 4. In some embodiments, each anti-TROP2 antibody, on average, is conjugated with 1-4 drug molecules, more specifically, with an average of 2 drug molecules.

In another embodiment, a drug-linker can be conjugated to an anti-TROP2 antibody by binding to the thiol group of a cysteine residue. Each anti-TROP2 antibody typically contains multiple cysteines, but many, if not all, of them form disulfite bonds between each other, and thus are not available for such conjugation. In some embodiments, therefore, one or more of the disulfide bonds of the anti-TROP2 antibody can be broken to form free thiol (SH) groups by reaction with a reducing reagent, such as 2-mercaptoethanol, dithiothreitol (DTT) or tris(2-carboxyethyl) phosphine (TCEP), for instance. The reaction can be monitored and/or controlled so that a sufficient number of disulfite bonds are broken to allow conjugation while maintaining a sufficient number of disulfide bonds to keep the structure stability of the anti-TROP2 antibody.

In some embodiments, the number of bonds formed between the drug-linker and cysteine residue on the anti-TROP2 antibody is from 1 to 10. In one embodiment, the number of such bonds is at least 1, or alternatively at least 2, or 4. In some embodiments, the number of such formed bonds is no more than 10, or alternatively no more than 9, or 8, 7, 6, 5, or 4. In one embodiment, each anti-TROP2 antibody, on average, is conjugated with 2-4 drug molecules through cysteines.

In some embodiments, drug molecules are conjugated to the anti-TROP2 antibody through a mixture of lysine and cysteine residues.

An anti-TROP2 antibody can be modified, by way of, e.g., site-specific mutagenesis, to introduce additional thiolated lysine or cysteine residues to allow suitable conjugation. Amino acid modification methods are well known in the art. Modified anti-TROP2 antibody can then be experimentally examined for their stability and antigen binding capability. In one embodiment, at least one thiolated lysine or cysteine residue is introduced by such modification. In another embodiment, at least two thiolated lysine or cysteine residues are introduced by such modification. In another embodiment, the Fc portion of the anti-TROP2 antibody is engineered with increased ADCC activity.

Drug Load

The drug load on an anti-TROP2 antibody may vary depending on many factors, such as the potency of the drug, the size, stability of the anti-TROP2 antibody, conjugatable groups available on the anti-TROP2 antibody, etc. In some embodiments, 1 to 10 maytansinoid drug molecules are conjugated with 1 anti-TROP2 antigen binding unit. In some embodiments, an average of 2 to 4 maytansinoid drug molecules are conjugated with 1 anti-TROP2 antigen binding unit. In some embodiments, an average of 2 maytansinoid drug molecules are conjugated with 1 anti-TROP2 antigen binding unit.

Metabolites of Maytansinoids-Linker-Anti-TROP2 Antibody Conjugates to Release the Effective Agents While not wishing to be bound to any theories, it is contemplated that upon endocytosis, compounds of any one of Formula Ia-Ic are degraded by intracellular proteins to metabolites comprising the maytansinoid moiety which are cytotoxic. In some embodiments, the compound is of Formula IVa, IVb or IVc:

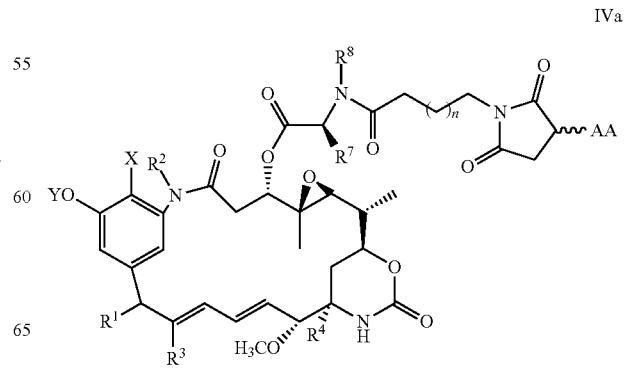

IVa

-continued

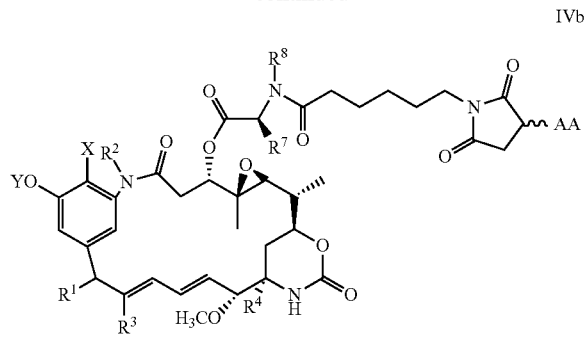

IVb

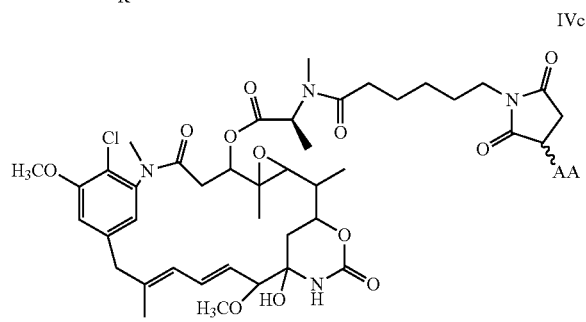

IVc or a salt thereof, wherein AA is selected from, but is not limited to

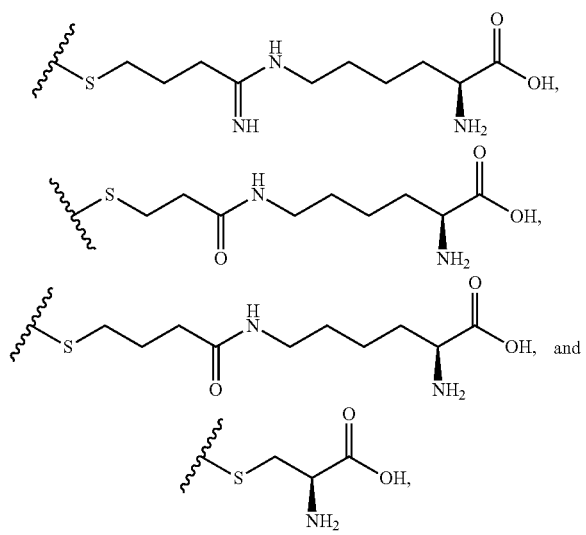

wherein ∿∿∿ represents point of connection to the rest of the molecule, and other variables are as defined herein.

Methods of Treatment

In another aspect, provided herein is a method of treating a proliferative, inflammatory or immunologic disease or condition in a patient in need thereof comprising administering an effective amount of one or more compounds as described herein, for example, a compound of any one of Formula Ia-Ic and IVa-IVc.

The compounds can be formulated as pharmaceutical compositions and administered to the patient in a variety of forms adapted to the chosen route of administration, i.e., orally or parenterally, by intravenous (IV.), intramuscular, topical or subcutaneous routes. The amount of the compounds will vary depend on the nature of the drug, linker, drug load, degree of cell surface triggered the internalization, trafficking, and release of the drug, the disease being treated, the conditions of the patient, such as age, gender, weight, etc. and can be determined by methods known to the art, for example, see U.S. Pat. No. 4,938,949, and will be ultimately at the discretion of the attendant physician or clinician.

In general, a suitable dose will be in the range of from about 0.1 to about 200 mg/kg, e.g., from about 0.5 to about 50 mg/kg of body weight I.V. infusion over 30-90 min every 1-4 week for 52 weeks, about 1.0 to about 25 mg/kg of body weight IV infusion over 30-90 min every 1-4 week for 52 weeks, about 1.5 to about 15 mg/kg body weight IV infusion over 30-90 min every 1-4 week for 52 weeks, or in the range of about 1 to 10 mg/kg body weight IV infusion over 30-90 min every 1-4 week. In some embodiments, the dose is from about 1.0 mg to about 100 mg/day, e.g., from about 2 mg to about 5 g per day, about 10 mg to about 1 g per day, about 20 to about 500 mg per day, or in the range of about 50 to 100 mg per day. The compounds can be administered daily, weekly, monthly, such as once a day, every 1-3 weeks, or month. Alternatively, the compounds can be administered in cycles, such as administered daily for a number of days, for example, 5 days to 21 days, with a period, such as one day to seven days, wherein no drug is being administered.

In some embodiments, the compound is administered at an initial dose of 1-4 mg/kg over 30-90 minute IV infusion, followed by 1-2 mg/kg over 30 minute I.V. infusion weekly or every 1-4 weeks for 52 weeks. In some embodiments, the compound is administered at an initial dose of 2-10 mg/kg over 30-90 minutes I.V. infusion, followed by 1-5 mg/kg over 30-90 minutes IV infusion every 1-4 weeks for 52 weeks.

In some embodiments, the compounds are administered in conjunction with another therapy. For example, the compounds can be co-administered with another therapy for treating cancer, for example, radiation therapy or another anticancer agent known in the art.

In another aspect, provided herein is a method of treating a proliferative, inflammatory or immunologic disease or condition in a patient in need thereof comprising administering an effective amount of a compound of Formula IVa, wherein the compound of Formula IVa is generated as a result of a metabolic chemical reaction following administration of a compound of Formula Ia, or a pharmaceutically acceptable salt thereof, to the patient.

In another aspect, provided herein is a method of treating a proliferative, inflammatory or immunologic disease or condition in a patient in need thereof comprising administering an effective amount of a compound of Formula IVb, wherein the compound of Formula IVb is generated as a result of a metabolic chemical reaction following administration of a compound of Formula Ib, or a pharmaceutically acceptable salt thereof, to the patient.

In another aspect, provided herein is a method of treating a proliferative, inflammatory or immunologic disease or condition in a patient in need thereof comprising administering an effective amount of a compound of Formula IVc, wherein the compound of Formula IVc is generated as a result of a metabolic chemical reaction following administration of a compound of Formula Ic, or a pharmaceutically acceptable salt thereof, to the patient.

Metabolic chemical reaction refers to a reaction occurring inside the body, for example, cells, or the subject, in which a chemical compound is converted to another chemical compound. The conversion can be by metabolic and/or chemical processes and can occur in one step or through a series of two or more steps. Metabolic chemical reactions include reactions of degrading a protein or peptide component of a maytansinoid linker anti-TROP2 antibody conjugate.

Pharmaceutical Compositions

In a further aspect, provided are pharmaceutical compositions comprising one or more compounds as described herein, for example, a compound of any one of Formula Ia-Ic, and one or more pharmaceutically acceptable carriers. Such compositions should contain at least 0.1% of active compound. The percentage of the compositions may vary and may be between about 2 to about 90% of the weight of a given unit dosage form. The amount of active compound in such therapeutically useful compositions is such that an effective dosage level will be obtained.

Examples of pharmaceutical compositions suitable for injection or infusion can include sterile aqueous solutions or dispersions in a pharmaceutically acceptable liquid carrier or vehicle, or sterile powders comprising the active ingredient which are adapted for the extemporaneous preparation of sterile injectable or infusible solutions or dispersions, optionally encapsulated in liposomes. Other forms of pharmaceutical compositions include topical formulations, such as gel, ointments, creams, lotions or transdermal patches, etc. The pharmaceutical compositions include using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

In a further aspect, provided are methods of producing a pharmaceutical composition comprising admixing a compound as described herein, for example, a compound of any one of Formula Ia-IVc, and a pharmaceutically acceptable carrier. Methods of admixing an active ingredient with a pharmaceutically acceptable carrier are generally known in the art, for example, uniformly mixing the active compound(s) with liquids or finely divided solid carriers, or both, in the required proportions, and then, if necessary, forming the resulting mixture into a desired shape.

In some embodiments, a compound of any one of Formula Ia-IVc is formulated as an injectable, for example, at a concentration of 2-50 mg/mL in an aqueous solution comprising 4-10 mg/mL sodium chloride and/or 5-12 mg/mL sodium acetate, or alternatively at a concentration of 2-50 mg/mL in an aqueous solution comprising 5-10 mg/mL sodium chloride, 1-5 mg/mL sodium phosphate dibasic heptahydrate, 0.1-0.5 mg/mL sodium phosphate monobasic monohydrate.

Other examples of formulations of a compound of any one of Formula Ia-IVc include an injectable formulation having a concentration of 2-100 mg/mL of the compound in an aqueous solution comprising 0.5-1.0% sodium chloride, 0.05-0.10% monobasic sodium phosphate dihydrate, 1.0-2.0% dibasic sodium phosphate dihydrate, 0.01-0.05% sodium citrate, 0.10-0.20% citric acid monohydrate, 1.0-2.0% mannitol, 0.1%-0.2 polysorbate 80, and Water for Injection, USP. Sodium hydroxide added as necessary to adjust pH.

Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Coupling reagents include carbodiimide, amininum and phosphonium based reagents. Carbodiimide type reagents include dicyclohexylcarbodiimide (DCC), diisopropylcarbodiimide (DIC), and 1-ethyl-3-(3-dimethylaminopropyl)-dicarbodiimide (EDC), etc. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxytris(pyrrolidino)phosphonium hexafluorophosphate (PyAOP) and benzotriazol-1-yl-N-oxy-tris(pyrrolidino)phosphonium hexafluorophosphate (PyBOP). Amide formation step may be conducted in a polar solvent such as dimethylformamide (DMF) and may also include an organic base such as diisopropylethylamine (DIEA) or dimethylaminopyridine (DMAP).

For example, compounds of Formula Ia or Ib can be prepared by contacting a compound of Formula A or B, respectively, wherein the variables are as defined herein, with an antibody in a suitable solvent, such as a buffer.

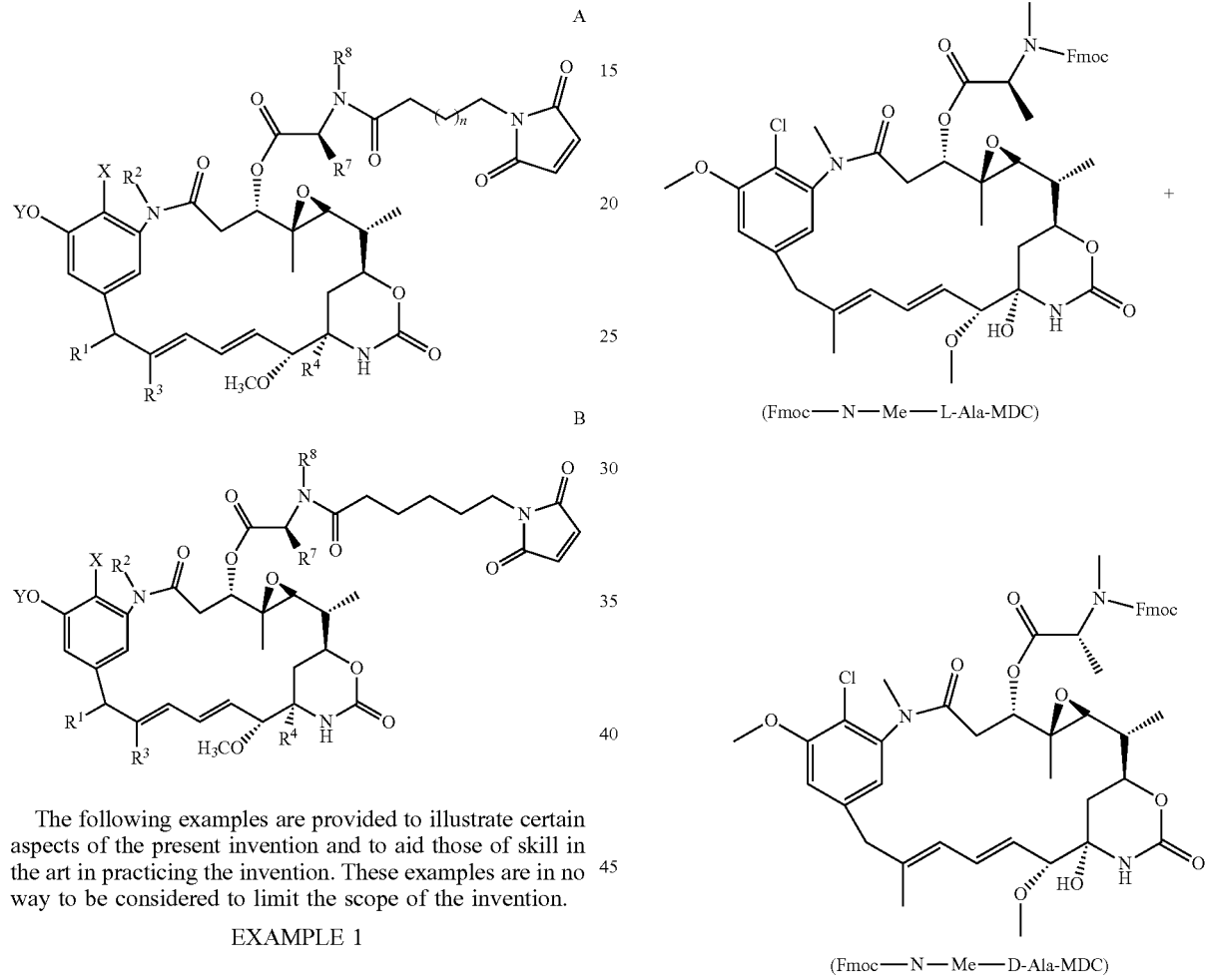

The following examples are provided to illustrate certain aspects of the present invention and to aid those of skill in the art in practicing the invention. These examples are in no way to be considered to limit the scope of the invention.

EXAMPLE 1

Esterification of Maytansinol with Fmoc-N-methyl-L-alanine (Fmoc-N-Me-D/L-Ala-MDC)

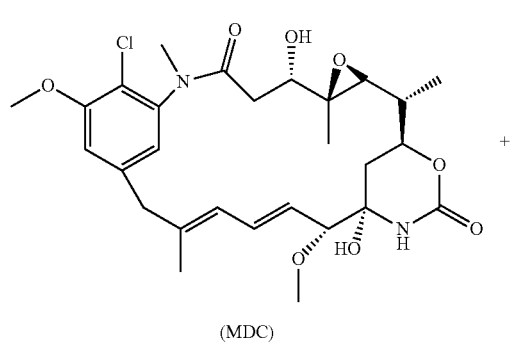

A mixture of maytansinol (0.600 g, 1.062 mmol), Fmoc-N-Me-L-Ala (6.911 g, 21.24 mmol), Sc(OTf)$_3$ (0.314 g, 0.637 mmol) and DMAP (0.389 g, 3.186 mmol) in CH$_2$Cl$_2$ (100 mL) under the protection of N2, then stirred for 0.5 h at −8° C. DIC (2.949 g, 23.37 mmol) was added dropwise, stirred for 0.5 h, warmed to r.t. slowly, filtered to recover the Lewis acid catalyst, the filtrate was quenched with diluted HCl and extracted with CH$_2$Cl$_2$. The combined organic phase was washed with NaHCO$_3$aq, brine, dried over anhydrous Na$_2$SO$_4$. The solvent was removed under reduced pressure. Chromatography (silica gel, CH$_2$Cl$_2$/MeOH 30:1) gave the desired product as a mixture of diastereomer Fmoc-N-Me-D/L-Ala-MDC: white solid (0.8385 g, 90.5%). Further column chromatography (silica gel, $CH_2Cl_2$/MeOH 100:1 to 20:1) gave two fractions as pure diastereomer. The higher Rf fraction was determined to be the D-aminoacyl ester diastereomer (Fmoc-N-Me-D-Ala-MDC), while the lower Rf fraction was the desired L-aminoacyl ester (Fmoc-N-Me-L-Ala-MDC). Fmoc-N-Me-L-Ala-MDC: white solid (0.4262 g, 46.0% yield), $^1$H NMR (400 MHz, $CDCl_3$): δ0.77 (3H, s), 1.22-1.32 (6H, m), 1.40-1.48 (1H, m), 1.63 (3H, s), 2.13 (1H, dd, J=14.4, 2.8 Hz), 2.53 (1H, dd, J=14.4, 10.8 Hz), 2.64 (3H, s), 2.88 (3H, s), 3.00 (1H, d, J=9.6 Hz), 3.07 (1H, d, J=12.4 Hz), 3.35 (3H, s), 3.48 (1H, d, J=8.8 Hz), 3.59 (1H, d, J=11.2 Hz), 3.97 (3H, s), 4.13-4.19 (1H, m), 4.15 (1H, s), 4.24 (1H, t, J=10.8 Hz), 4.72-4.77 (2H, m), 5.03 (1H, q, J=6.8 Hz), 5.65 (1H, dd, J=15.2, 9.2 Hz), 6.29 (1H, br), 6.41 (1H, dd, J=15.2, 11.2 Hz), 6.52 (1H, d, J=1.2 Hz), 6.70 (1H, d, J=10.8 Hz), 6.79 (1H, d, J=1.2 Hz), 7.33 (1H, t, J=7.6 Hz), 7.36 (1H, t, J=7.6 Hz), 7.39 (1H, d, J=7.6 Hz), 7.49 (1H, d, J=7.6 Hz), 7.70 (1H, d, J=7.6 Hz), 7.72 (1H, d, J=7.6 Hz). LC-MS (M+Na$^+$) calc.: 894.3, found: 894.3. Fmoc-N-Me-D-Ala-MDC: white solid (0.3993 g, 43.1% yield), $^1$H NMR (400 MHz, $CDCl_3$): δ0.84 (3H, s), 1.22-1.27 (3H, m), 1.40-1.48 (1H, m), 1.51 (3H, d, J=7.6 Hz), 1.67 (3H, s), 2.20 (1H, dd, J=14.4, 2.8 Hz), 2.63 (1H, dd, J=14.4, 12.4 Hz), 2.85 (1H, d, J=9.6 Hz), 2.96 (3H, s), 3.17 (3H, s), 3.20 (1H, s), 3.24 (3H, s), 3.40 (1H, d, J=9.2 Hz), 3.51 (1H, d, J=12.8 Hz), 3.99 (3H, s), 4.20-4.28 (2H, m), 4.38-4.43 (2H, m), 4.80-4.98 (2H, m), 5.80 (1H, dd, J=15.2, 11.2 Hz), 6.18 (1H, s), 6.25 (1H, d, J=10.8 Hz), 6.40 (1H, dd, J=15.2, 11.2 Hz), 6.79 (1H, d, J=1.6 Hz), 6.84 (1H, d, J=1.6 Hz), 7.32 (2H, t, J=7.6 Hz), 7.41 (2H, t, J=7.6 Hz), 7.61 (2H, d, J=7.6 Hz), 7.77 (2H, d, J=7.6 Hz). LC-MS (M+Na$^+$) calc.: 894.3, found: 894.3.

EXAMPLE 2

Deprotection of Fmoc-N-Me-D/L-Ala-MDC (N-Me-D/L-Ala-MDC)

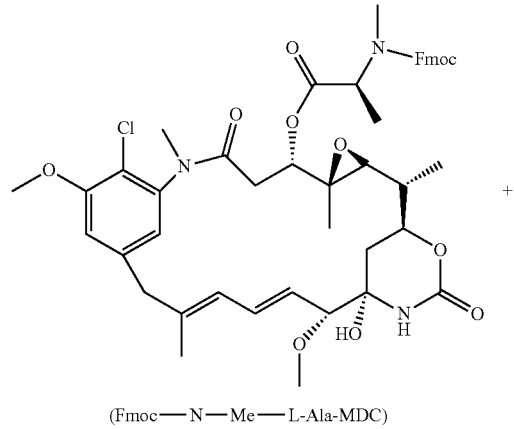

(Fmoc—N—Me—L-Ala-MDC)

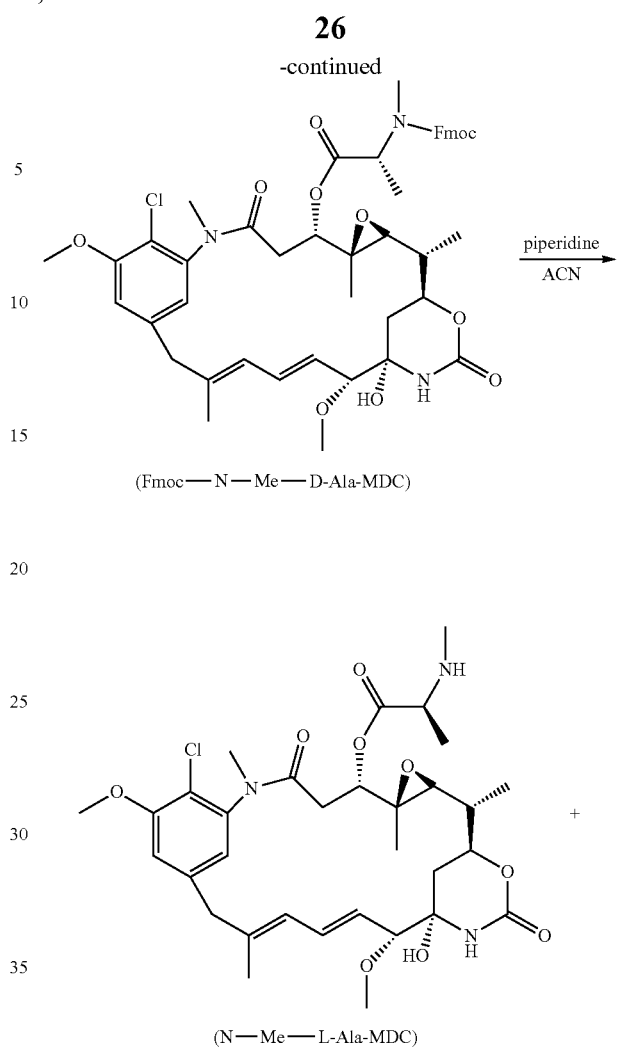

Into Fmoc-N-Me-D/L-Ala-MDC (0.463 g, 0.5307 mmol) in ACN (200 mL) was added piperidine (0.865 g, 10.15 mmol). The mixture was stirred at r.t. for 4 h, quenched with water and extracted with $CH_2Cl_2$. The combined organic phase was washed with brine and dried over Na$_2$SO$_4$. The solvent was removed under reduced pressure to give the crude product, which was used in the next step without further purification. LC-MS (M+H$^+$) calc.: 650.3, found: 650.3. Rt: 3.96 min.

EXAMPLE 3

Deprotection of Fmoc-N-Me-L-Ala-MDC (N-Me-L-Ala-MDC)

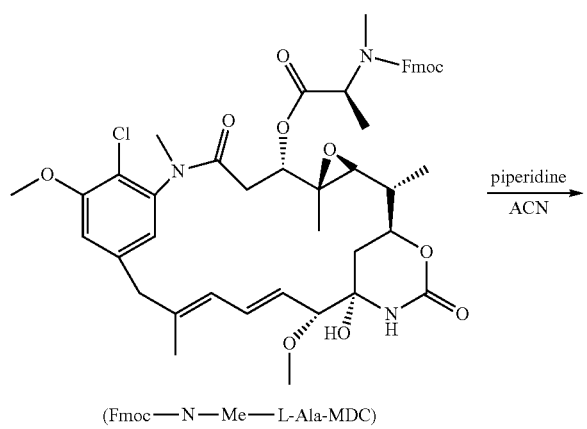

(Fmoc—N—Me—L-Ala-MDC)

piperidine / ACN →

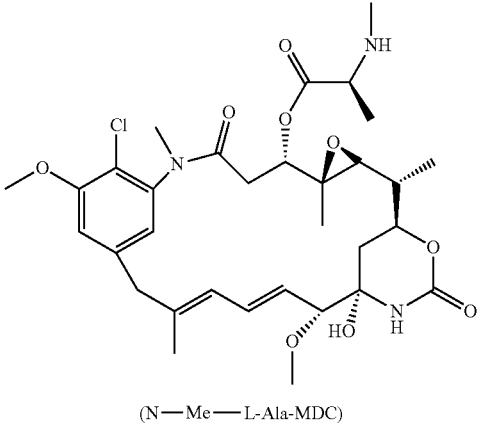

(N—Me—L-Ala-MDC)

Into Fmoc-N-Me-L-Ala-MDC (0.463 g, 0.5307 mmol) in ACN (200 mL) was added piperidine (0.865 g, 10.15 mmol). The mixture was stirred at r.t. for 4 h, quenched with water and extracted with CH$_2$Cl$_2$. The combined organic phase was washed with brine and dried over Na$_2$SO$_4$. The solvent was removed under reduced pressure to give the crude product, which was used in the next step without further purification. LC-MS (M+H$^+$) calc.: 650.3, found: 650.3. Rt: 3.96 min.

EXAMPLE 4

Condensation of N-Me-D/L-Ala-MDC with MA-ACP (D-3AA-MDC and L-3AA-MDC)

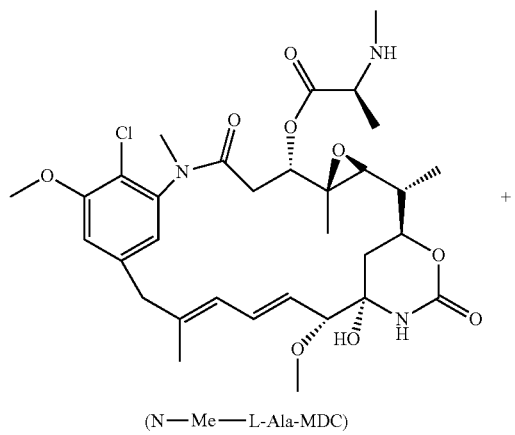

(N—Me—L-Ala-MDC)

+

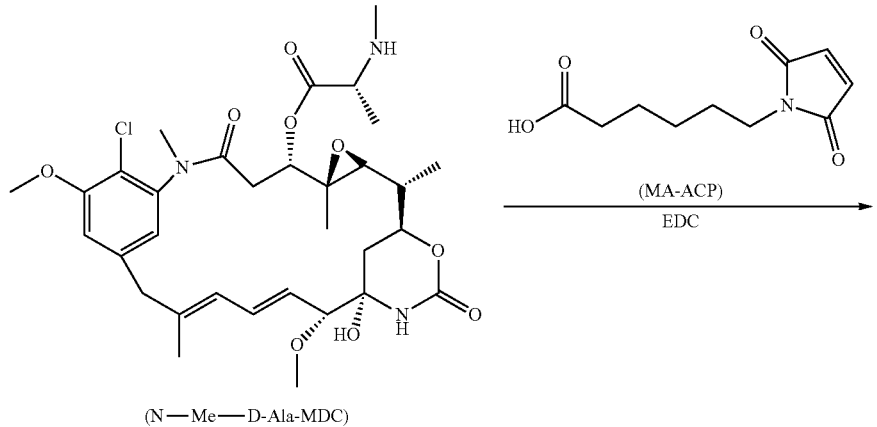

(N—Me—D-Ala-MDC)          (MA-ACP)
                              EDC →

-continued

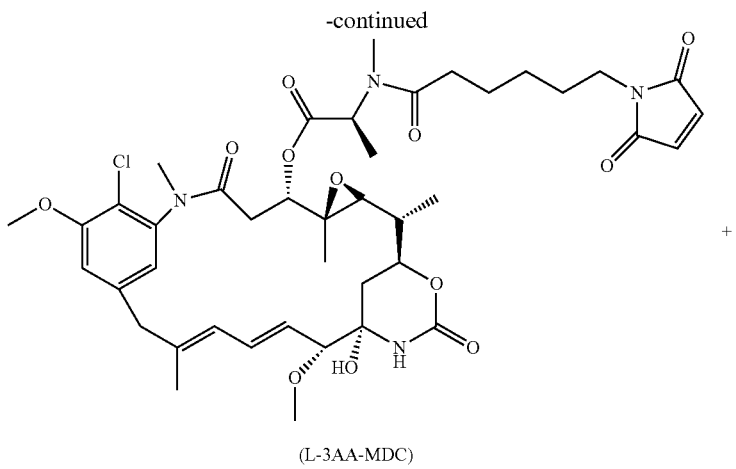

(L-3AA-MDC)

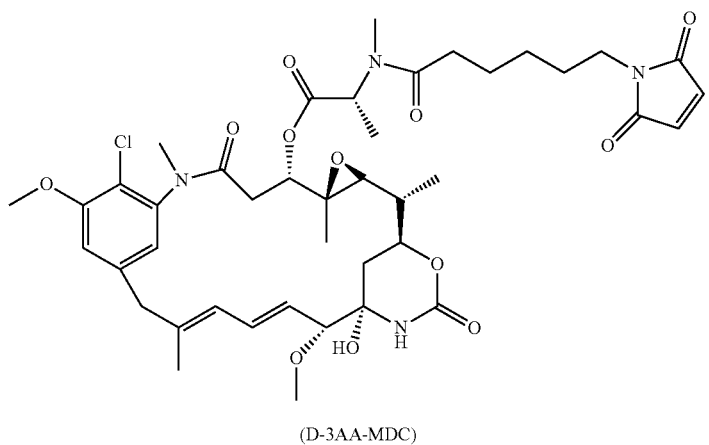

(D-3AA-MDC)

Into above prepared N-Me-D/L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, and dried over $Na_2SO_4$. The solvent was removed under reduced pressure. Chromatography (silica gel: $CH_2Cl_2$/MeOH 30:1) gave the crude product. Further purification by preparative HPLC on a YMC C-18 column (250×20 mm, S 10 μm) gave two fractions (Rt=6.59 min and 6.98 min) as white solid. The higher Rt fraction was determined to be the D-aminoacyl ester diastereomer (D-3AA-MDC, 45.2%), while the lower Rt fraction was the desired L-aminoacyl ester (L-3AA-MDC, 54.8%). L-3AA-MDC: white solid (0.1364 g, 30.5% overall yield over two steps), $^1$H NMR (400 MHz, $CDCl_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3, found: 865.3. Rt: 6.59 min. D-3AA-MDC: white solid (0.1128 g, 25.2% overall yield over two steps), $^1$H NMR (400 MHz, $CDCl_3$): δ0.86 (3H, s), 1.22-1.38 (4H, m), 1.25 (3H, d, J=9.2 Hz), 1.38-1.45 (1H, m), 1.48 (3H, d, J=7.6 Hz), 1.56-1.70 (4H, m), 1.68 (3H, s), 1.75 (1H, d, J=13.6 Hz), 2.19 (1H, dd, J=14.4, 2.8 Hz), 2.28-2.36 (2H, m), 2.65 (1H, dd, J=14.2, 12.0 Hz), 2.80 (1H, d, J=9.6 Hz), 3.01 (3H, s), 3.19 (1H, d, J=13.2 Hz), 3.32 (3H, s), 3.42 (1H, d, J=9.6 Hz), 3.47-3.54 (3H, m), 3.98 (3H, s), 4.29 (1H, t, J=10.4 Hz), 4.88 (1H, dd, J=11.8, 3.2 Hz), 5.07 (1H, q, J=7.6 Hz), 5.84 (1H, dd, J=15.2, 9.2 Hz), 6.23 (1H, d, J=11.2 Hz), 6.27 (1H, s), 6.41 (1H, dd, J=15.2, 11.2 Hz), 6.69 (2H, s), 6.79 (1H, d, J=1.2 Hz), 6.84 (1H, d, J=1.2 Hz). LC-MS (M+Na$^+$) calc.: 865.3, found: 865.3. Rt: 6.98 min.

EXAMPLE 5

Condensation of N-Me-L-Ala-MDC with MA-ACP (L-3AA-MDC)

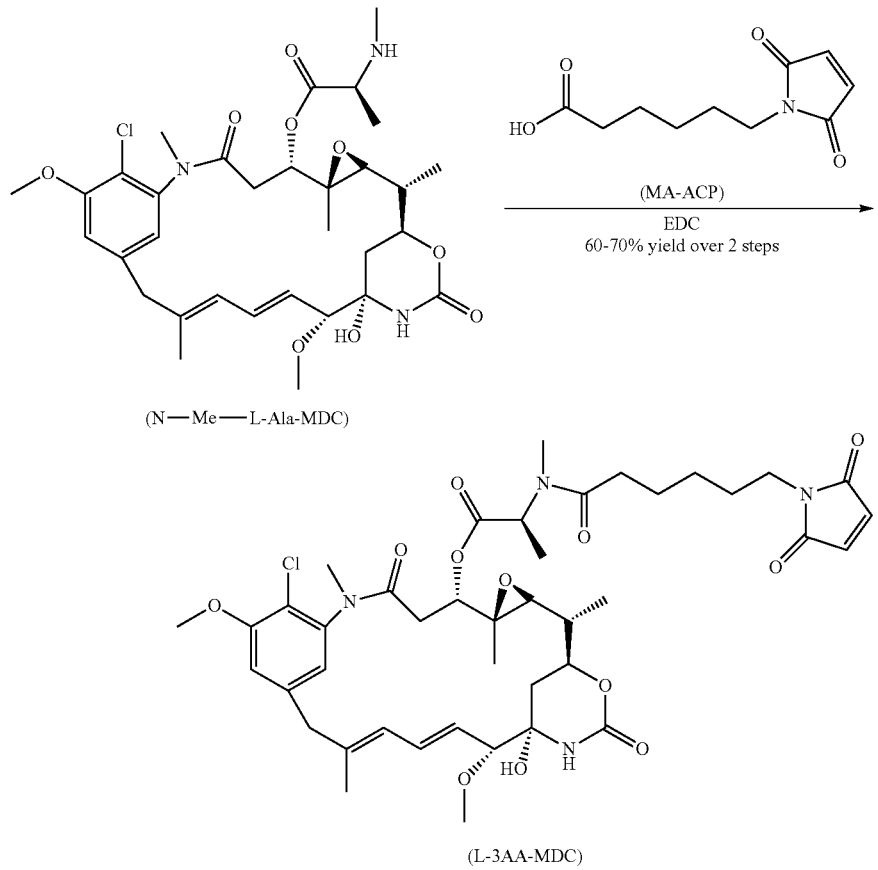

(N—Me—L-Ala-MDC)

(MA-ACP)
EDC
60-70% yield over 2 steps (L-3AA-MDC)

Into above prepared N-Me-L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, dried over $Na_2SO_4$. The solvent was removed under reduced pressure. Chromatography (silica gel: $CH_2Cl_2$/MeOH 30:1) gave the crude product. Further purification by preparative HPLC on a YMC C-18 column (250×20 mm, S 10 μm) gave the desired L-3AA-MDC: white solid (0.280 g, 62.6% overall yield over two steps), $^1$H NMR (400 MHz, $CDCl_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3, found: 865.3. Rt: 6.59 min.

EXAMPLE 6

Recombinant Antibody Expression and Purification

The anti-TROP2 antibody was produced in CHO cells essentially as described in Wood et al., *J Immunol.* 145:3011 (1990). Briefly, each of the antibody genes was constructed with known molecular biology techniques (Molecular Cloning: A Laboratory Manual, 3rd edition J. Sambrook et al., Cold spring Harbor Laboratory Press). Wherein the light and heavy chain nucleotide sequence of the BAT0806 antibody was shown in SEQ ID NO: 1 and SEQ ID NO: 2, respectively. And the light and heavy chain nucleotide sequences of BAT0807 and BAT0808 was shown in SEQ ID NO: 3 and SEQ ID NO: 4, respectively. A derivative cell line(CHO-BAT) of Chinese Hamster Ovary cell line CHO-K1(ATCC #CCL-61) was used as the host cell. The method of constructing the high yield and stable cell line is described as follows: the host cell was grown in CD-CHO media (GIBCO). Transfections were facilitated using electroporation. Host cells in logarithmic growth phase were harvested by centrifugation and then resuspended in fresh CD-CHO media to achieve a cell densities of approximately 1×10$^7$ cells (600 uL) per cuvette, then add the linearized plasmid 40 g and mix well, wherein the CHO-BAT cell line were used as the host cell for BAT0806 and BAT0807 expression vectors and the CHO-BAT-KF (knockout fucose) cell line for BAT0808 expression vector. Suspensions of cells containing 40 g of linearized plasmid DNA were electroporated at 960 μFD and 300V, seeding 1.25×10$^3$ cells per well in 96-well tissue culture plates containing a suitable selection drug. The antibody expression level in the culture supernatant of clones isolated on 96-well tissue culture plates was determined by an enzyme-linked immunosorbent assay (ELISA). On the basis of the antibody titer in the supernatant, clones with high-level expression were transferred to 24-well plate (Corning) containing suitable media. Specific antibody productivity (qAb) and specific growth rate (μ) were further analyzed by seeding cells at 2×10$^5$ cells per well containing 5 mL of medium in six-well tissue culture plates, culturing for 2 and 4 days, and usually 20-30 high-producing clones (parental clones) were transferred to shake flask for successive selection. 5-8 of the highest yield clones were chosen for further subcloning and expression tests.

In some embodiments, the anti-Trop2 antibody provided by the present invention may be BAT0806, which comprise a light chain amino acid sequence as shown in SEQ ID NO: 1 and a heavy chain amino acid sequence as shown in SEQ ID NO: 2. In some embodiments, the anti-Trop2 antibodies provided by the present invention may be BAT0807 or BAT0808, which comprise a light chain amino acid sequence as shown in SEQ ID NO: 3 and a heavy chain amino acid sequence as shown in SEQ ID NO: 4, or an equivalent thereof.

The purification was carried out by centrifuging the cell suspension and harvesting the supernatant, which was further cleared by centrifuging. Protein A affinity columns such as Mab Select SuRe (GE Healthcare) and ion exchange such as Capto S (GE) were used to purify the expressed antibodies.

EXAMPLE 7

Conjugation of Anti-TROP2 Antibody BAT0806 with 3AA-MDC

The anti-TROP2 antibody BAT0806 was diluted to 8.0 mg/mL with solution A (20 mM phosphate, 100 mM NaCl and 2 mM EDTA, pH 7.4), and then reduced with TCEP (3.2 molar equivalent). This step was followed by incubation for 60 minutes at 37° C., ultrafiltration, and exchange with solution B (10 mM succinic acid, 2 mM EDTA, pH 7.4). Sulfhydryl antibody was assayed by measuring the absorbance of the reaction product of sulfydryl and DTNB (5,5'-dithiobis(2-nitrobenzoic acid), Aldrich company) at 412 nm, and then determining the concentration of thiol.

The concentration of DMA was 10% in the conjugate reaction. 3AA-MDC was prepared as in Examples 4 and 5. The ratio of 3AA-MDC to sulfhydryl was 1.5:1.0 (molar equivalent). 3AA-MDC was added to the reduced antibody, and stirred for 3 hours at room temperature, then 5 mM cysteine was added to the mixture with continued stirring for 0.5 hour. The final reaction mixture was purified by cation exchange column, then ultrafiltered with a 0.22 micron filter, and stored at −80° C. The antibody concentration, aggregation and the coupling drug ratio of Batansine-0806 were measured by ultraviolet absorption, dimensional exclusion chromatography and reverse high performance liquid chromatography, respectively. All monoclonal antibodies and ADCs from this application had a purity of more than 98%.

EXAMPLE 8

Conjugation of Anti-TROP2 Antibody BAT0806 with CL2A-SN-38

The anti-TROP2 antibody BAT0806 was diluted to 8.0 mg/mL with solution A (20 mM phosphate, 100 mM NaCl and 2 mM EDTA, pH 7.4), and then reduced with TCEP (3.2 molar equivalent). This step was followed by incubation for 60 minutes at 37° C., ultrafiltration and exchange with solution B (10 mM succinic acid, 2 mM EDTA, pH 7.4). Sulfhydryl antibody was assayed by measuring the absorbance of the reaction product of sulfydryl and DTNB (5,5'-dithiobis(2-nitrobenzoic acid), Aldrich company) at 412 nm, and then determining the concentration of thiol.

The concentration of DMSO was 10% in the conjugate reaction. The ratio of CL2A-SN-38 to sulfhydryl was 1.5:1.0 (molar equivalent). CL2A-SN-38 was added to the reduced antibody, and stirred for 3 hours at room temperature, then 5 mM cysteine was added with continued stirring for 0.5 hour. The reaction mixture was purified by cation exchange column, then ultrafiltered with a 0.22 micron filter, and stored at −80° C. The antibody concentration, aggregation and the coupling drug ratio of BAT0806-CL2A-SN-38 were measured by ultraviolet absorption, dimensional exclusion chromatography and reverse high performance liquid chromatography, respectively. All monoclonal antibodies and ADCs from this application had a purity of more than 98%.

EXAMPLE 9

Conjugation of Anti-TROP2 Antibody BAT0807 with 3AA-MDC

The anti-TROP2 antibody BAT0807 was diluted to 8.0 mg/mL with solution A (20 mM phosphate, 100 mM NaCl and 2 mM EDTA, pH 7.4), and then completely reduced with excess TCEP (3.2 molar equivalent). This step was followed by incubation for 60 minutes at 37° C., ultrafiltration and exchange with solution B (10 mM succinic acid, 2 mM EDTA, pH 7.4). Sulfhydryl antibody was assayed by measuring the absorbance of the reaction product of sulfydryl and DTNB (5,5'-dithiobis(2-nitrobenzoic acid), Aldrich company) at 412 nm, then determining the concentration of thiol. Later, oxidation reactions were mediated by excessive copper sulfate (CuSO4) or dehydrogenated ascorbic acid (dHAA) to reconnect the disulfide bond between antibody chains, such that site-mutated cysteine(s) were preserved.

The concentration of DMA was 10% in the conjugate reaction. 3AA-MDC was prepared as in Examples 4 and 5. The ratio of 3AA-MDC to sulfhydryl was 1.5:1.0 (molar equivalent). 3AA-MDC was added to the reduced antibody, and stirred for 3 hours at room temperature, then 5 mM cysteine was added and stirring continued for 0.5 hour. The reaction mixture was purified by cation exchange column, then ultrafiltered with a 0.22 micron filter, and stored at −80° C. The antibody concentration, aggregation and the coupling drug ratio of Batansine-0807 were measured by ultraviolet absorption, dimensional exclusion chromatography and reverse high performance liquid chromatography, respectively. All monoclonal antibodies and ADCs from this application had a purity of more than 98%.

EXAMPLE 10

Conjugation of Anti-TROP2 Antibody BAT0808 with 3AA-MDC

The anti-TROP2 antibody BAT0808 was diluted to 8.0 mg/mL with solution A (20 mM phosphate, 100 mM NaCl and 2 mM EDTA, pH 7.4), and then completely reduced with excess TCEP (3.2 molar equivalent). This step was followed by incubation for 60 minutes at 37° C., ultrafiltration and exchange with solution B (10 mM succinic acid, 2 mM EDTA, pH 7.4). Sulfhydryl antibody was assayed by measuring the absorbance of the reaction product of sulfydryl and DTNB (5,5'-dithiobis(2-nitrobenzoic acid), Aldrich company) at 412 nm, then determining the concentration of thiol. Later, oxidation reactions were mediated by excessive copper sulfate (CuSO4) or dehydrogenated ascorbic acid (dHAA) to reconnect the disulfide bond between antibody chains, and site-mutated cysteine(s) were preserved.

The concentration of DMA was 10% in the conjugate reaction. 3AA-MDC was prepared as in Examples 4 and 5. The ratio of 3AA-MDC to sulfhydryl was 1.5:1.0 (molar equivalent). 3AA-MDC was added to the reduced antibody, and stirred for 3 hours at room temperature, 5 mM cysteine was then added with continued stirring for 0.5 hour. The reaction mixture was purified by cation exchange column, then ultrafiltered with a 0.22 micron filter, and stored at −80° C. The antibody concentration, aggregation and the coupling drug ratio of Batansine-0808 were measured by ultraviolet absorption, dimensional exclusion chromatography and reverse high performance liquid chromatography, respectively. All monoclonal antibodies and ADCs from this application had a purity of more than 98%.

EXAMPLE 11

Proliferation Inhibitory Effect of Antibody-Drug Conjugate Batansine-0806

The Proliferation Inhibitory effects of Batansine-0806 were evaluated on different derived TROP2 positive tumor cell lines MDA-MB-468, N87 and A431. In short, MDA-MB-468, A431 and N87 cells were digested with 0.25% (volume/volume) trypsin, stripping the cells from the cell culture flask, centrifuged and then resuspended with complete medium. Then, MDA-MB-468 or A431 cells were seeded into the wells of 96-well plates at a density of 5000 cells/hole/100 μl, and N87 cells were seeded at 8000 cells/well/100 μl. The cells were cultured at 37° C. overnight, and then 100 μl of culture medium containing different concentrations of Batansine-0806 was added to the cell cultures. After 72 hours of incubation, the 96-well plates were washed with PBS (pH 7.4). Cell counting kit-8 (CCK8) reagents were used to analyze relative cell proliferation. As shown in FIG. 7, FIG. 8, FIG. 9 and FIG. 10A, antibody-drug conjugate Batansine-0806 significantly inhibited the proliferation of TROP2 positive cell lines MDA-MB-468, A431 and N87 with an EC50 at 3.21 nM, 0.53 nM and 0.34 nM respectively, while naked antibody BAT0806 has no effect on the proliferation of MDA-MB-468.

EXAMPLE 12

Proliferation Inhibitory Effect of Antibody-Drug Conjugate Batansine-0807

Figure 7:
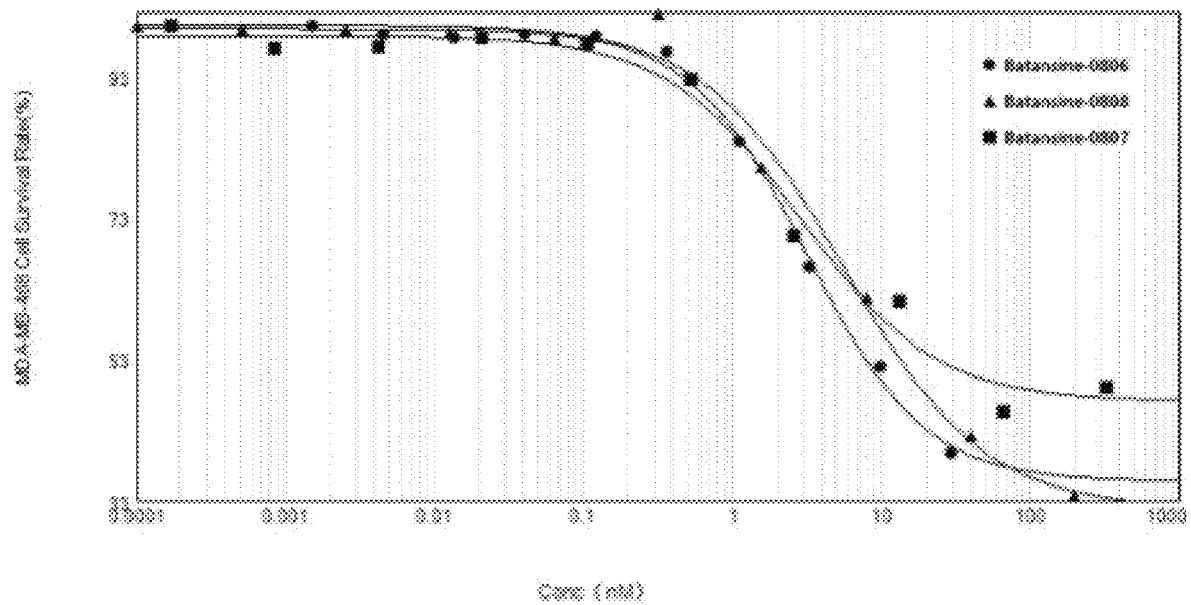
FIG. 7 shows the Proliferation Inhibitory effect of Batansine-0806, Batansine-0807 and Batansine-0808 towards MDA-MB-468 cells.
Figure 8:
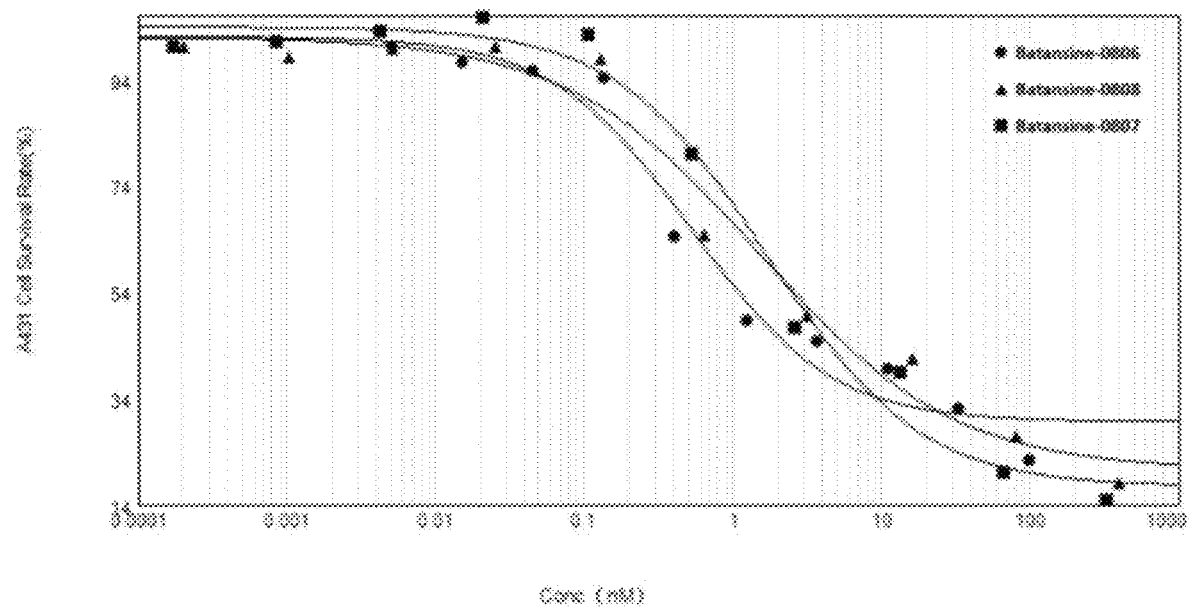
FIG. 8 shows the Proliferation Inhibitory effect of Batansine-0806, Batansine-0807 and Batansine-0808 towards A431 cells.
Figure 9:
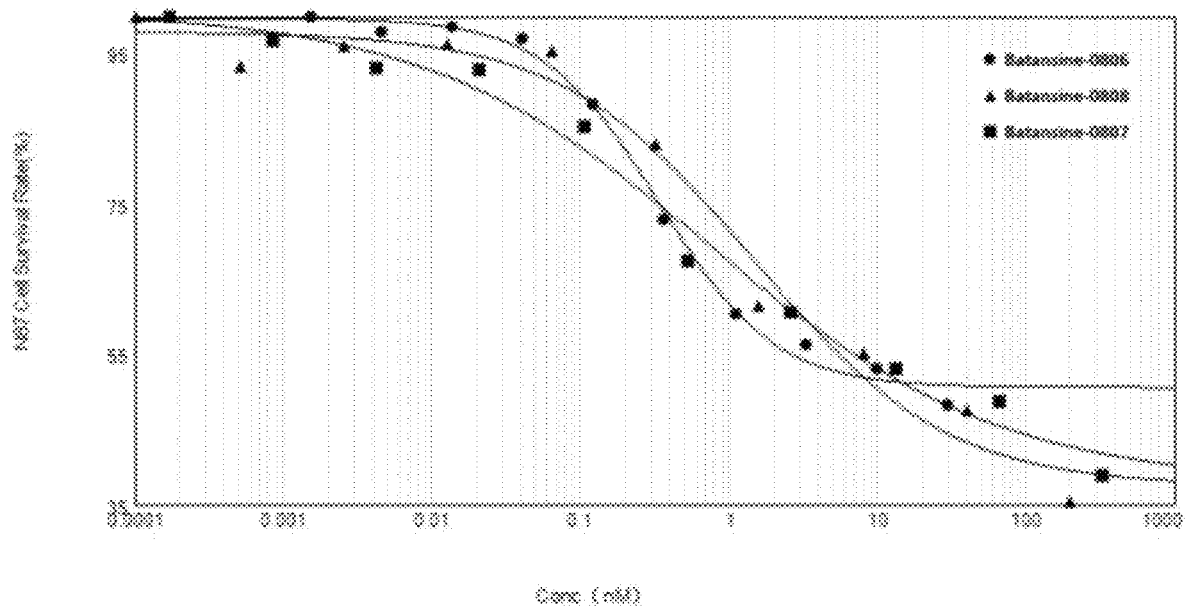
FIG. 9 shows the Proliferation Inhibitory effect of Batansine-0806, Batansine-0807 and Batansine-0808 towards N87 cells.
Figure 10A:
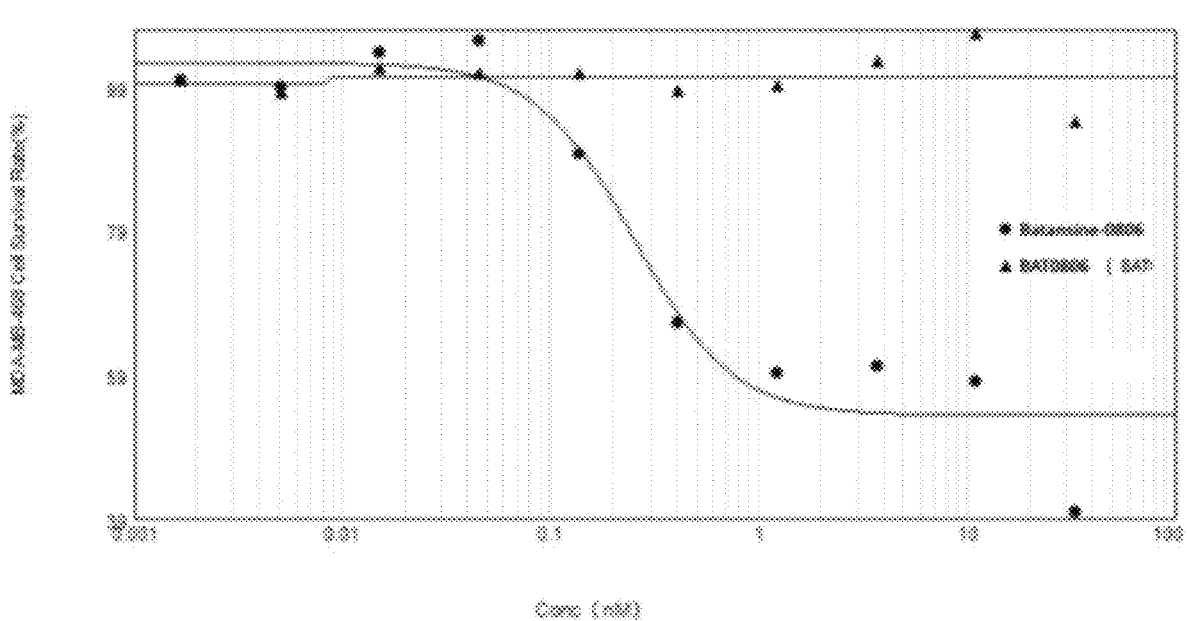
FIGS. 10A and 10B show that unconjugated anti-TROP2 antibody BAT0806 or BAT0808 have no Proliferation Inhibitory effect on MDA-MB-468 cells.
Figure 10B:
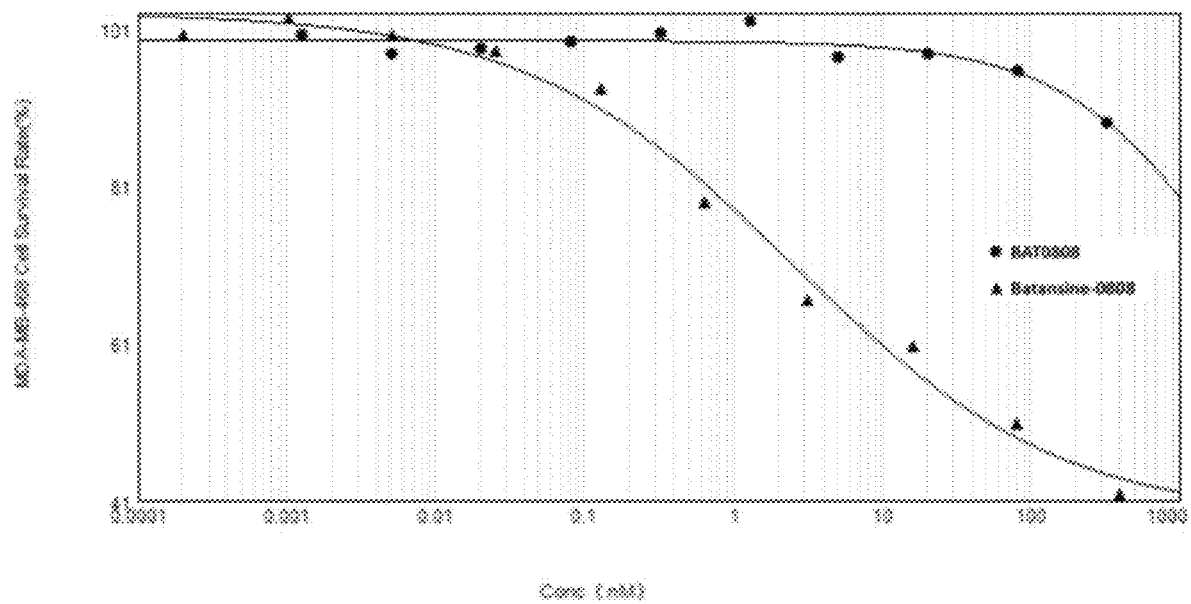

The Proliferation Inhibitory effects of Batansine-0807 were evaluated on different derived TROP2 positive tumor cell lines MDA-MB-468, N87 and A431. In short, MDA-MB-468, A431 and N87 cells were digested with 0.25% (volume/volume) trypsin, stripping the cells from the cell culture flask, centrifuged and then resuspended with complete medium. Then, MDA-MB-468 or A431 cells were seeded into the wells of 96-well plates at a density of 5000 cells/hole/100 μl, and N87 cells were seeded at 8000 cells/well/100 μl. The cells were cultured at 37° C. overnight, and then 100 μl of culture medium containing different concentrations of Batansine-0807 was added to the cell cultures. After 72 hours of incubation, the 96-well plates were washed with PBS (pH 7.4). Cell counting kit-8 (CCK8) reagents were used to analyze relative cell proliferation. As shown in FIG. 7, FIG. 8 and FIG. 9, antibody-drug conjugate Batansine-0807 significantly inhibited the proliferation of TROP2 positive cell lines MDA-MB-468, A431 and N87 with an EC50 at 2.89 nM, 1.73 nM and 0.77 nM respectively.

EXAMPLE 13

Proliferation Inhibitory Effect of Antibody-Drug Conjugate Batansine-0808

The Proliferation Inhibitory effects of Batansine-0808 were evaluated on different derived TROP2 positive tumor cell lines MDA-MB-468, N87 and A431. In short, MDA-MB-468, A431 and N87 cells were digested with 0.25% (volume/volume) trypsin, stripping the cells from the cell culture flask, centrifuged and then resuspended with complete medium. Then, MDA-MB-468 or A431 cells were seeded into the wells of 96-well plates at a density of 5000 cells/hole/100 μl, and N87 cells were seeded at 8000 cells/well/100 μl. The cells were cultured at 37° C. overnight, and then 100 μl of culture medium containing different concentrations of Batansine-0808 was added to the cell cultures. After 72 hours of incubation, the 96-well plates were washed with PBS (pH 7.4). Cell counting kit-8 (CCK8) reagents were used to analyze relative cell proliferation. As shown in FIG. 7, FIG. 8, FIG. 9 and FIG. OB, antibody-drug conjugate Batansine-0808 significantly inhibited the proliferation of TROP2 positive cell lines MDA-MB-468, A431 and N87 with an EC50 at 5.61 nM, 1.53 nM and 1.47 nM respectively, while naked antibody BAT0808 has no remarkable effect on the proliferation of MDA-MB-468.

EXAMPLE 14

The Comparison of the Proliferation Inhibitory Effect of the Antibody-Drug Conjugate Batansine-0808 and BAT0806-CL2A-SN-38

Figure 11A:
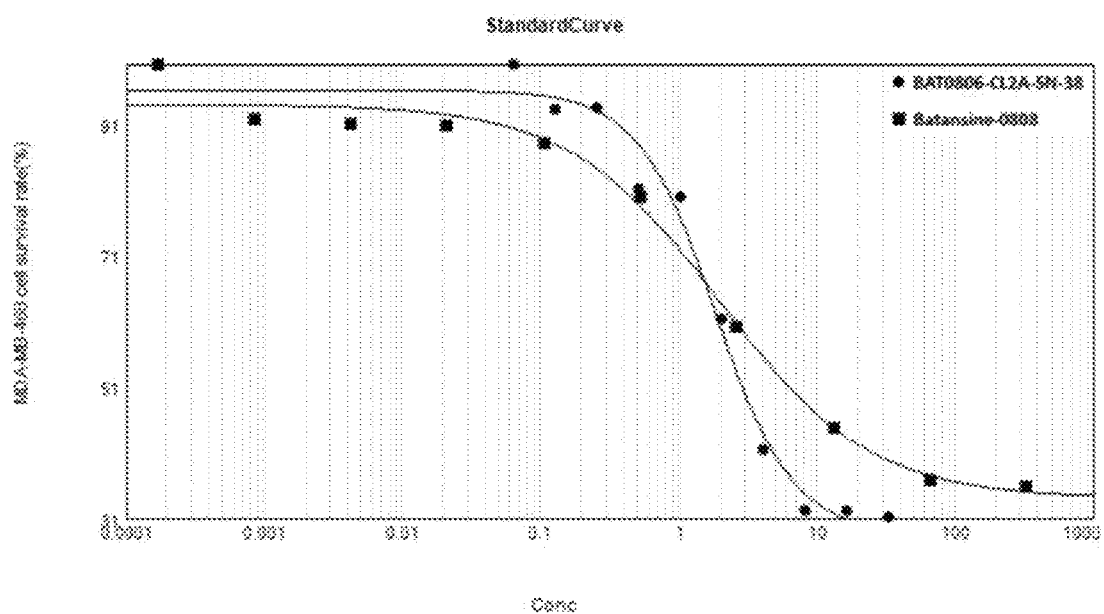
FIGS. 11A, 11B and 11C show the cell proliferation Inhibitory effect of Batansine-0808 and BAT0806-CL2A-SN-38 towards MDA-MB-468, A431 and N87 cells.
Figure 11B:
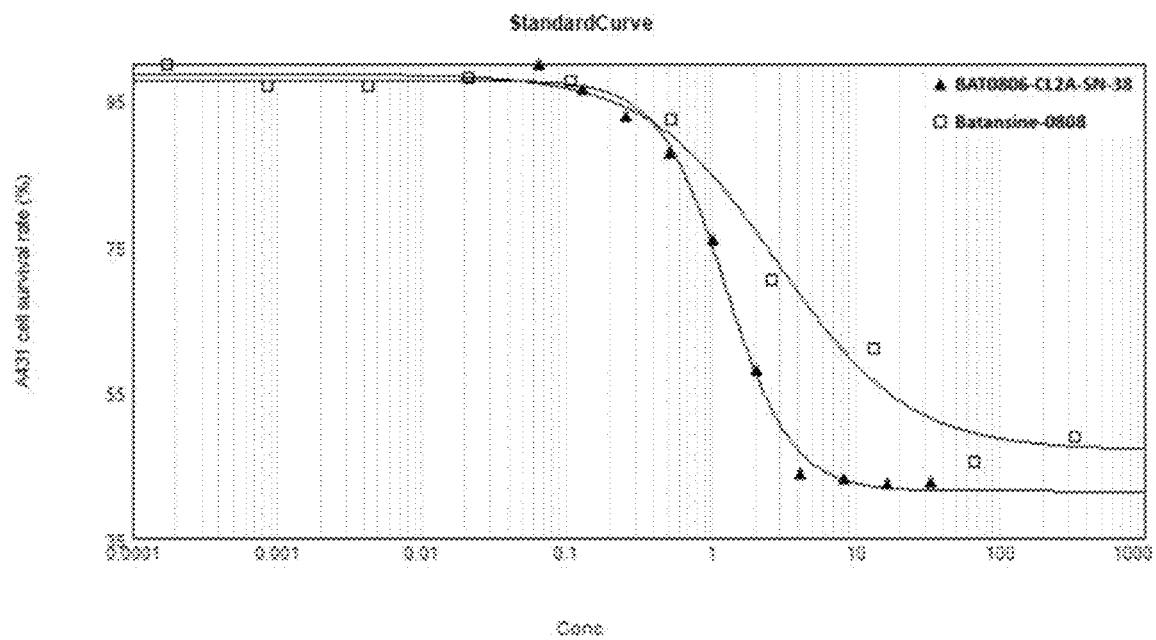
Figure 11C:
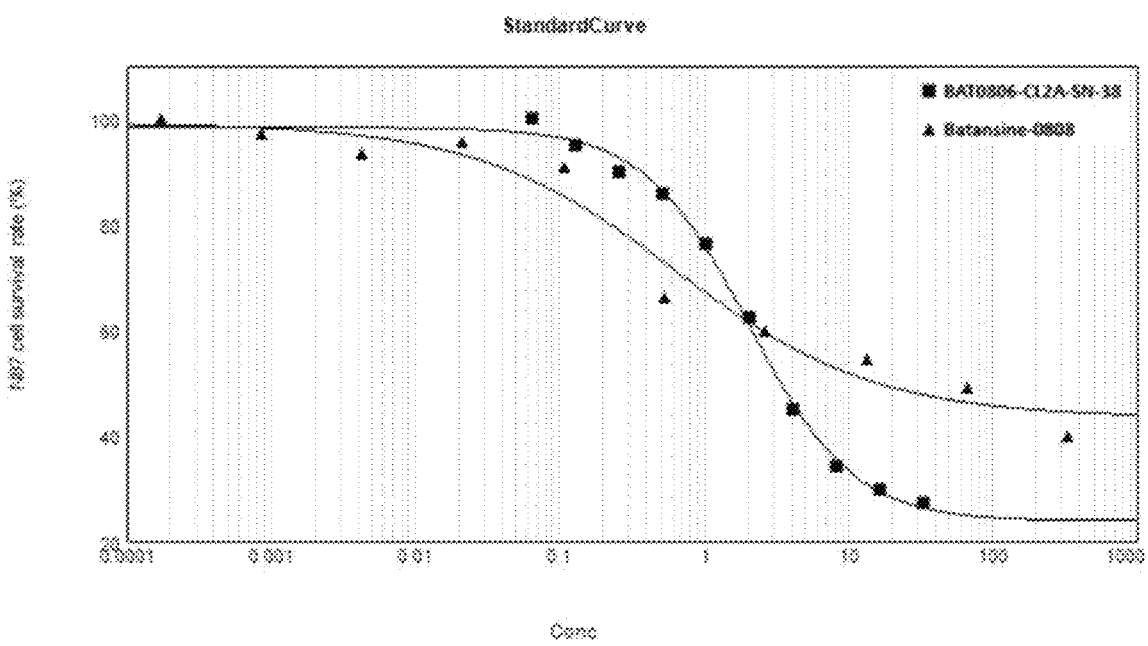

The comparison of the proliferation Inhibitory effect of the antibody-drug conjugate Batansine-0808 and BAT0806-CL2A-SN-38 were evaluated on different derived TROP2 positive tumor cell lines MDA-MB-468, N87 and A431. In short, MDA-MB-468, A431 and N87 cells were digested with 0.25% (volume/volume) trypsin, stripping the cells from the cell culture flask, centrifuged and then resuspended with complete medium. Then, MDA-MB-468 or A431 cells were seeded into the wells of 96-well plates at a density of 5000 cells/hole/100 μl, and N87 cells were seeded at 8000 cells/well/100 μl. The cells were cultured at 37° C. overnight, and then 100 μl of culture medium containing different concentrations of Batansine-0808 was added to the cell cultures. After 72 hours of incubation, the 96-well plates were washed with PBS (pH 7.4). Cell counting kit-8 (CCK8) reagents were used to analyze relative cell proliferation. As shown in FIG. 11A, FIG. 11B, and FIG. 11C, the EC50 of the antibody-drug conjugate Batansine-0808 and BAT0806-CL2A-SN-38 on the TROP2 positive cell lines MDA-MB-468, A431 and N87 were at the same level.

EXAMPLE 15

The Enhanced ADCC Effect of Batansine-0808

Figure 12A:
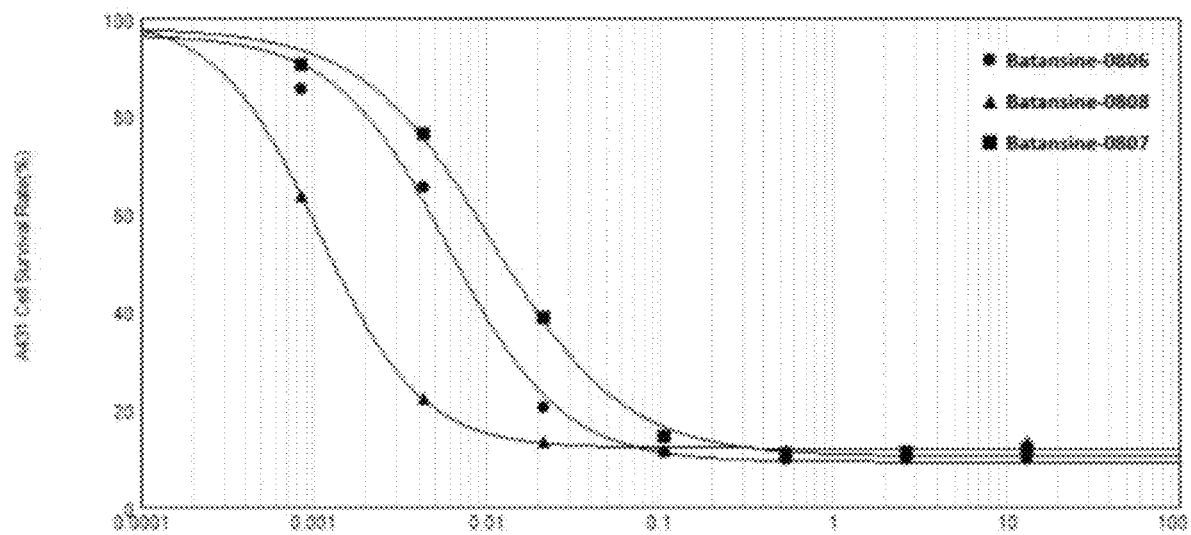
FIGS. 12A and 12B shows the enhancement of Batansine-0808 mediated Antibody Dependent Cell Cytotoxicity effect. Compared with Batansine-0806, Batansine-0807 and BAT0806-CL2A-SN-38, Batanine-0808 significantly inhibited the proliferation of the human TROP2 positive skin cancer cell A431 at a much lower concentration.
Figure 12B:
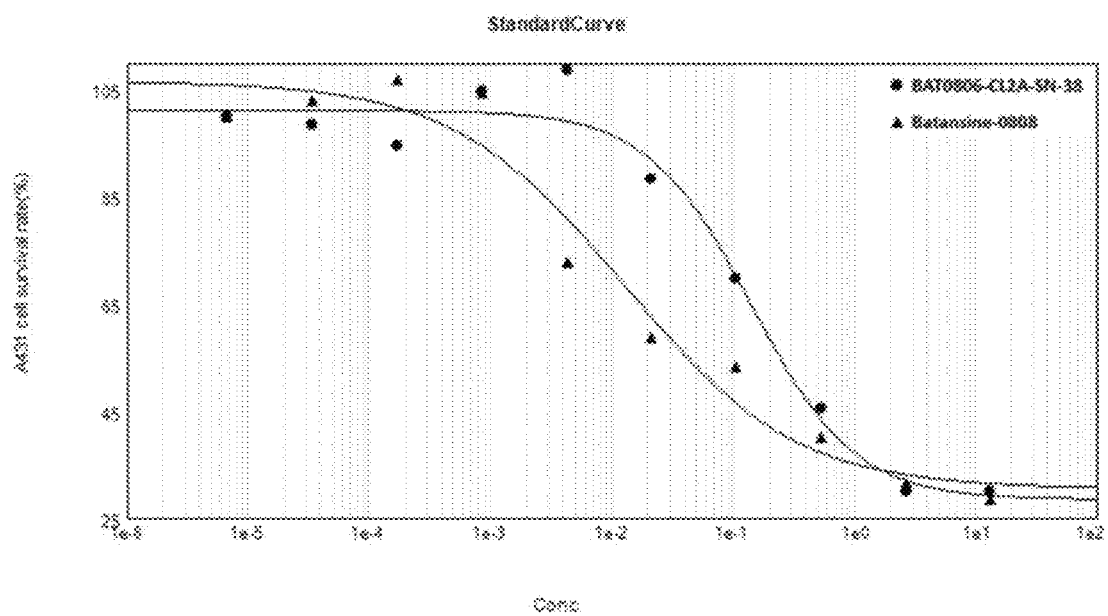

The enhanced ADCC characteristic of Batansine-0808 was evaluated through Proliferation Inhibition assay on TROP2 positive human skin carcinoma cell line A431. Target cell were resuspended in DMEM-F12 medium contain 2% FBS. The cell concentration was adjusted to $1 \times 10^5$ cells/ml and 50 µl cells/well were seeded in a 96-well plate (5000 cells/well). Antibody-drug conjugate samples were diluted with DMEM-F12 medium contain 2% FBS (The initial concentration was 8 µg/ml, then serially diluted by the ratio of 1:5. Two duplicate wells were set for each concentration. Eight gradients were set up. The final ADC concentrations were 2, 0.4, 0.88, and 0.016, 0.0032, 0.00064, 0.000128, 0 µg/ml). Then, 50 µl/well of differing concentrations of antibody-drug conjugate samples were added to the wells seeded with cells, followed by incubation at 37° C., 5% $CO_2$ for 30 min. PBMC cells were centrifuged for 5 minutes at 800 r/min, washed twice with DMEM-F12 medium contain 2% FBS, and then the cell concentration was adjusted to $2 \times 10^5$ cells/ml. The PBMC cells were added to the seeded cells at 100 µl/well resulting in a final ratio of 10:1 or 5:1 of PBMC cells to target cells. The 96-well plates were incubated at 37° C. and 5% $CO_2$ for 72 h. The plates were washed twice with PBS (pH 7.5). Cell counting kit-8 (CCK8) reagents were used to analyze relative cell proliferation. As shown in FIG. 12A and FIG. 12B, at the same conditions compared with Batansine-0806, Batansine-0807 or BAT0806-CL2A-SN-38, Batansine-0808 significantly inhibited the proliferation of A431 cells, even at a much lower concentrations.

The inventors tested the Proliferation Inhibitory ability of three anti-TROP2 antibody-drug conjugates on three different tumor cell lines, and were surprised to find that different antibody modifications and different ways of drug coupling significantly influenced sensitivity of tumor cells to those conjugates. For example, if only Proliferation Inhibitory activity was studied, traditionally-coupled Batansine-0806 was found to be superior to site-specific coupled Batansine-0807 and Batansine-0808. Further, the EC50 value of Batansine-0806 was observed to be about 2-5 times lower than both of the latter two antibody-drug conjugates. When taking ADCC effects into consideration at the same time, the inventors were amazed to find that the cell Proliferation Inhibitory activity of Batansine-0808 was 5 to 10 times superior to Batansine-0806, Batansine-0807 or BAT0806-CL2A-SN-38 (shown in the table below).

| Cell line | EC50 (nM) | |
| --- | --- | --- |
| Cell proliferation | Batansine-0808 | BAT0806-CL2A-SN-38 |
| MDA-MB-468 | 1.95 | 1.84 |
| A431 | 2.89 | 1.26 |
| N87 | 0.56 | 1.84 |

| synergistic ADCC | Batansine-0806 | Batansine-0807 | Batansine-0808 | BAT0806-CL2A-SN-38 |
| --- | --- | --- | --- | --- |
| A431(10:1[a]) | 0.006 | 0.011 | 0.001 | / |
| A431(5:1[a]) | / | / | 0.130 | 0.143 |

[a]PBMC cell:Target cell

EXAMPLE 16

Cytotoxicity of Antibody-Drug Conjugate Batansine-0808 and BAT0806-CL2A-SN-38 on Human Normal Liver Cell Line LO2

Figure 13:
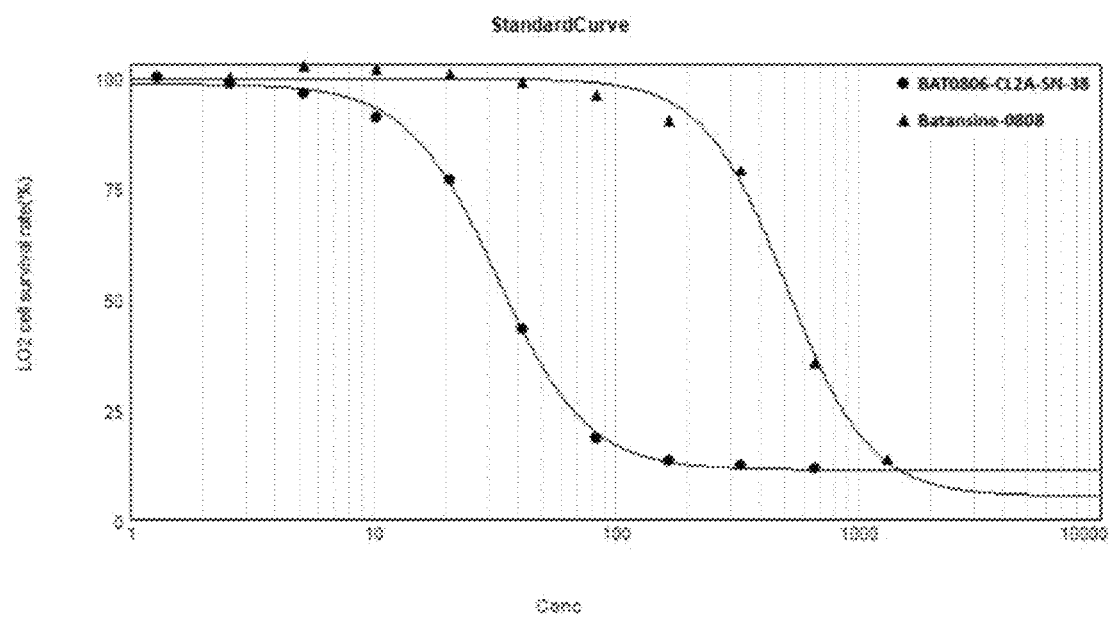
FIG. 13 shows the cytotoxicity of Batansine-0808 and BAT0806-CL2A-SN-38 on human normal liver cell line LO2.

The Cytotoxicity of Batansine-0808 and BAT0806-CL2A-SN-38 were evaluated on TROP2 negative human normal liver cell line LO2. In short, LO2 cells were digested with 0.25% (volume/volume) trypsin, stripping the cells from the cell culture flask, centrifuged and then resuspended with complete medium. Then, cells were seeded into the wells of 96-well plates at a density of 5000 cells/hole/100 µl. The cells were cultured at 37° C. overnight, and then 100 µl of culture medium containing different concentrations of Batansine-0808 and BAT0806-CL2A-SN-38 was added to the cell cultures. After 72 hours of incubation, the 96-well plates were washed with PBS (pH 7.4). Cell counting kit-8 (CCK8) reagents were used to analyze relative cell proliferation. As shown in FIG. 13, the EC50 of the antibody-drug conjugate BAT0806-CL2A-SN-38 was much lower than that of Batansine-0808(32.74 nM compare 511.3 nM), which means that the BAT0806-CL2A-SN-38 was more toxicity than Batansine-0808, at least in this cell line.

EXAMPLE 17

Figure 14A:
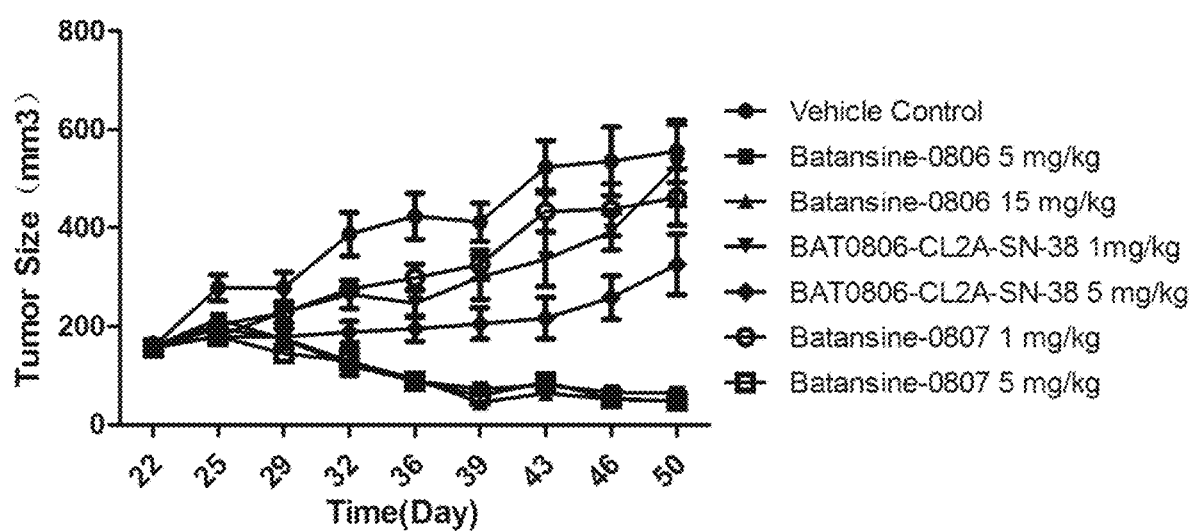
FIGS. 14A and 14B show that antibody drug conjugates Batansine-0806, Batansine-0807 and BAT0806-CL2A-SN-38 eradicated human MDA-MB-468 tumor in mouse xenografts.
Figure 14B:
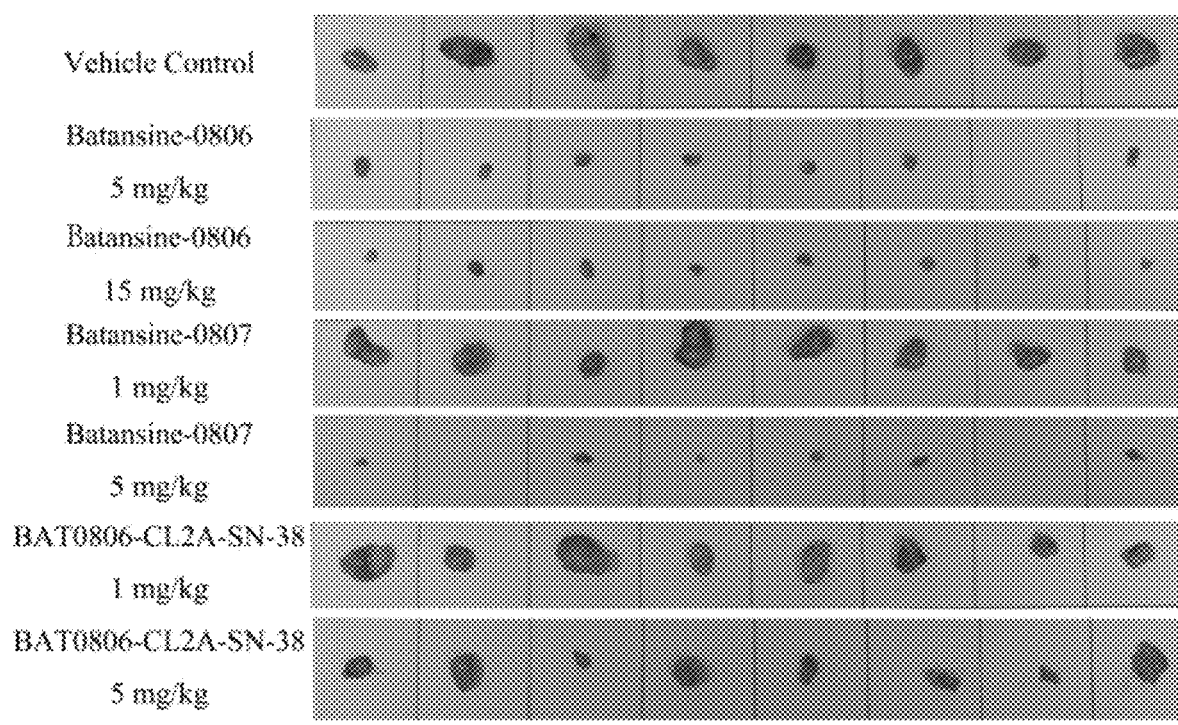

Batansine-0806, Batansine-0807 and BAT0806-CL2A-SN-38 Eradicates Human MDA-MB-468 Tumor Xenografts The effects of these anti-TROP2 antibody-drug conjugates on the growth of established tumors were examined on human MDA-MB-468 tumor xenografts. In brief, human MDA-MB-468 cells (Shanghai Cell Bank of the Chinese Academy of Sciences) were cultured in RPMI1640 medium supplemented with 10% FBS and 2 mM Glutamine. Harvested MDA-MB-468 cells were resuspended in PBS, and adjusted to a concentration of $5 \times 10^7$ cells per 100 µl. Female BALB/c nude mice, 8-9 weeks old, were injected subcutaneously with 200 µl of tumor cells in the right axillary. When the tumor xenograft size reached 150-200 $mm^3$ (calculated as $0.5 \times (length \times width^2)$), animals were randomly divided into groups. Animals were then treated with Batansine-0806 (5 or 15 mg/kg, i.v), Batansine-0807 (1 or 5 mg/kg, i.v) or BAT0806-CL2A-SN-38 (1 or 5 mg/kg, i.v). Animals were dosed once per week for a total of 4 doses i.v. at a dosage of 10 µL/g. Each group consisted of 10 mice. Tumor size was measured twice a week. 49 days after the first dose, animals were euthanized and tumors were removed and weighed. As shown in FIGS. 14A and 14B, rapid tumor shrinkage was observed with Batansine-0806 (5 or 15 mg/kg) and Batansine-0807 (5 mg/kg) from as early as Day 25. On the other hand, tumor size was continually growing when BAT0806-CL2A-SN-38 was dosed at 5 mg/kg. In addition, site-specific conjugated Batansine-0807 showed comparable effects to Batansine-0806 at a dose of 5 mg/kg, despite Batansine-0806 demonstrating better effects in vitro.

EXAMPLE 18

Figure 15A:
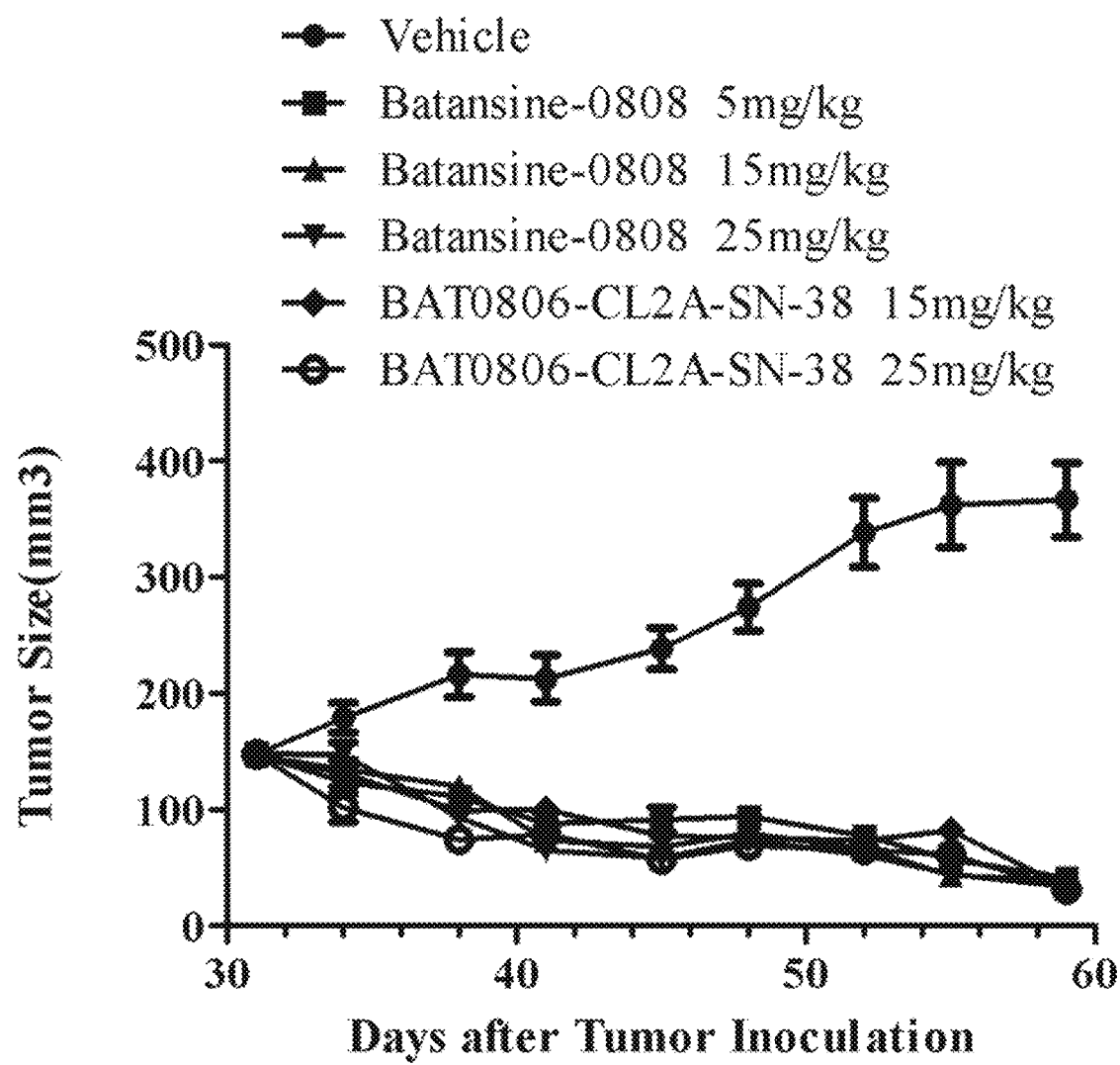
FIGS. 15A and 15B show that antibody drug conjugates Batansine-0808 and BAT0806-CL2A-SN-38 eradicated human MDA-MB-468 tumor in mouse xenografts.
Figure 15B:
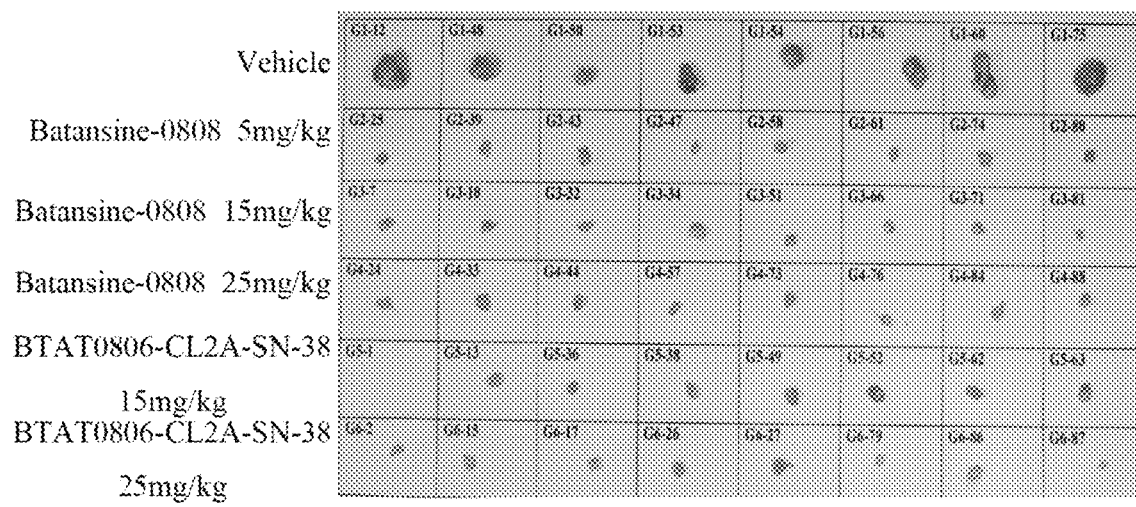

Batansine-0808 and BAT0806-CL2A-SN-38 Eradicates Human MDA-MB-468 Tumor Xenografts The effects of these anti-TROP2 antibody-drug conjugates on the growth of established tumors were examined on human MDA-MB-468 tumor xenografts. In brief, human MDA-MB-468 cells (Shanghai Cell Bank of the Chinese Academy of Sciences) were cultured in RPMI1640 medium supplemented with 10% FBS and 2 mM Glutamine. Harvested MDA-MB-468 cells were resuspended in PBS, and adjusted to a concentration of $5 \times 10^7$ cells per 100 µl. Female BALB/c nude mice, 8-9 weeks old, were injected subcutaneously with 200 µl of tumor cells in the right axillary. When the tumor xenograft size reached 150-200 $mm^3$ (calculated as 0.5×(length×width²)), animals were randomly divided into groups. Animals were then treated with Batansine-0808 (5, 15 or 25 mg/kg, i.v) or BAT0806-CL2A-SN-38 (15 or 25 mg/kg, i.v). Animals were dosed once per week for a total of 4 doses i.v. at a dosage of 10 μL/g. Each group consisted of 8 mice. Tumor size was measured twice a week. 28 days after the first dose, animals were euthanized and tumors were removed and weighed. As shown in FIGS. 15A and 15B, rapid tumor shrinkage was observed in all groups of Batansine-0808 (5 or 15 mg/kg) or BAT0806-CL2A-SN-38 (15 or 25 mg/kg, i.v) sine the first dose, and the tumor size of all the treated group are approximately when the experiment ended.

EXAMPLE 19

Batansine-0808 Eradicates Human MX-1 Tumor Xenografts

Figure 16:
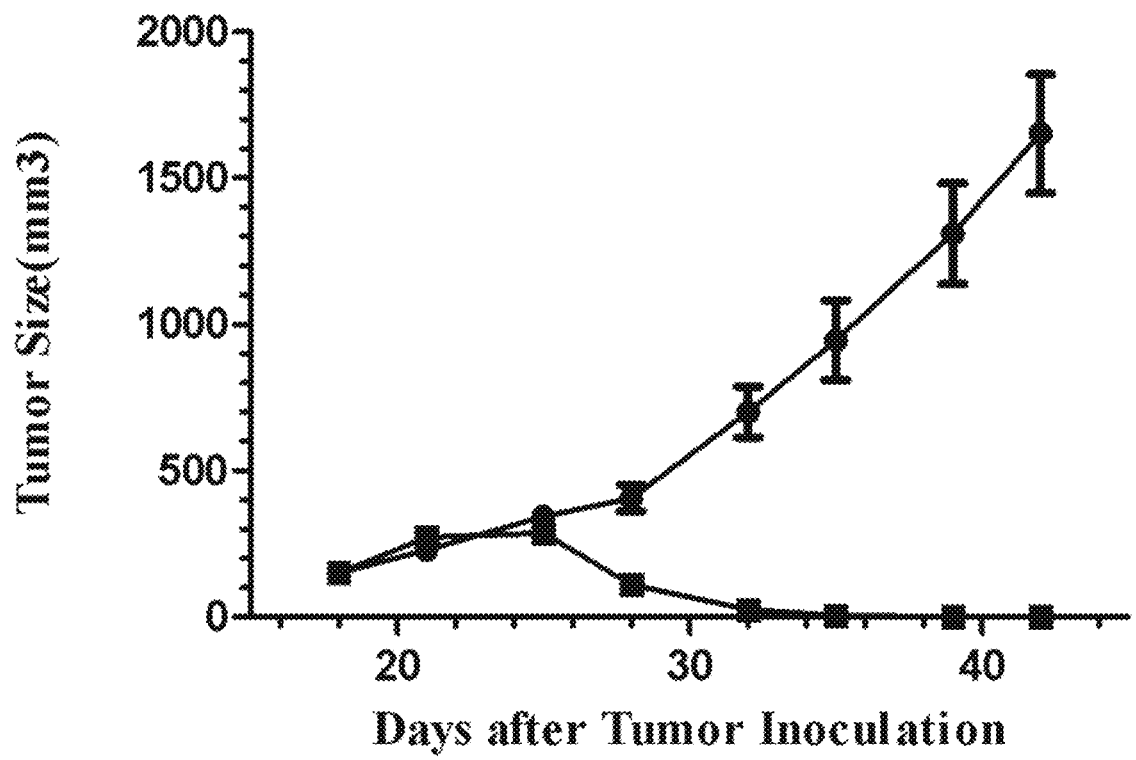
FIG. 16 shows that antibody drug conjugates Batansine-0808 eradicated human MX-1 tumor in mouse xenografts.

The effects of these anti-TROP2 antibody-drug conjugates on the growth of established tumors were examined on human MX-1 tumor xenografts. In brief, human MX-1 cells (Shanghai Cell Bank of the Chinese Academy of Sciences) were cultured in RPMI1640 medium supplemented with 10% FBS. Harvested MX-1 cells were resuspended in PBS, and adjusted to a concentration of $5 \times 10^7$ cells per 100 μl. Female BALB/c nude mice, 8-9 weeks old, were injected subcutaneously with 200 μl of tumor cells in the right axillary. When the tumor xenograft size reached 150-200 mm³ (calculated as 0.5×(length×width²)), animals were randomly divided into groups. Animals were then treated with Batansine-0808 (25 mg/kg, i.v) or same volume vehicle. Animals were dosed once per week for a total of 4 doses i.v. at a dosage of 10 μL/g. Each group consisted of 6 mice. Tumor size was measured twice a week. Administration was stopped at 28 day after first dose and observation continued until day 42. As shown in FIG. 16, rapid tumor shrinkage was observed with Batansine-0808 group as early as Day 26 and finally disappeared at the day 42 in all animals.

What is claimed is:

1. A compound of Formula Ia:

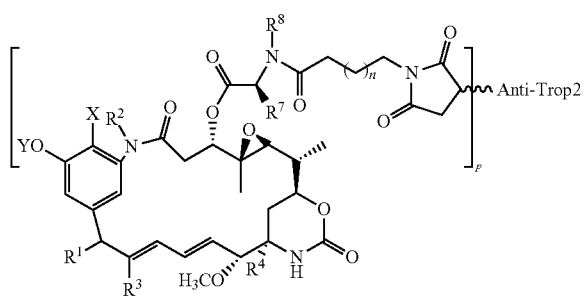

or a salt or solvate thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_1$-$C_6$ alkyl;
n is 0, 1, 2, 3, 4, 5, 6, 7 or 8;
p is selected from 1, 2, 3, 4, 5, 6, 7, 8, 9, 10; and
Anti-TROP2 is an anti-TROP2 (TACSTD2) antibody comprising a light chain comprising an amino acid sequence as shown in SEQ ID NO: 3, and a heavy chain comprising an amino acid sequence as shown in SEQ ID NO: 4.

2. The compound of claim 1, which is a compound of Formula Ib

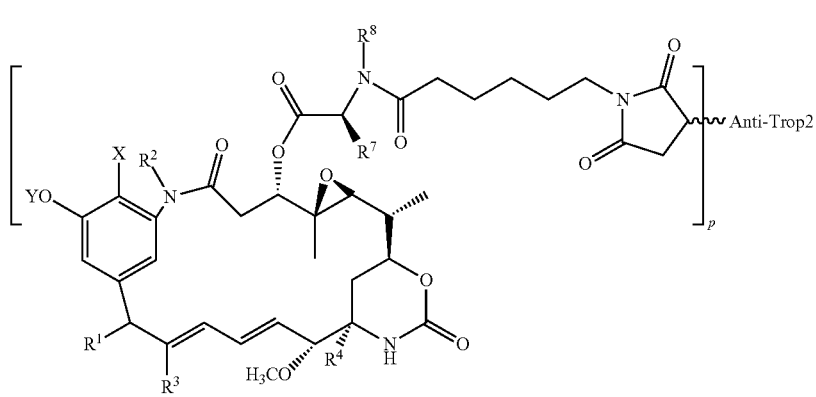

or a pharmaceutically acceptable salt or solvate thereof.

3. The compound of claim 1, which is a compound of Formula Ic

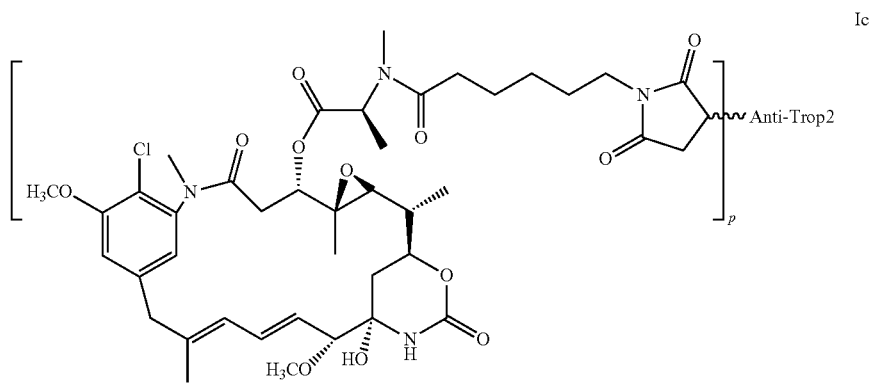

or a pharmaceutically acceptable salt or solvate thereof.

4. The compound of claim 1, wherein the anti-TROP2 antibody has a fucose content of 0-5%.

5. The compound of claim 4, wherein the anti-TROP2 antibody is expressed by an α-(1,6)-fucosyltransferase knocked out CHO cell line.

6. The compound of claim 1, wherein p is 2.

7. A pharmaceutical composition comprising a compound of claim 1.

8. A method of treating a proliferative disease or condition characterized by TROP2 positive cells in a patient in need thereof comprising administering to the patient an effective amount of the compound of claim 1.

9. The method of claim 8, which further comprises adding a second or third antibody enhancing immune surveillance activity to produce more effective treatment.

10. The method of claim 8, wherein the proliferative disease or condition characterized by TROP2 positive cells is selected from glioblastoma, medulloblastoma, urothelial carcinoma, breast cancer, head and neck cancer, kidney cancer, ovarian cancer, Kaposi's sarcoma, pancreatic cancer and lung cancer.

11. The compound of claim 9, wherein the second or third antibody is an antibody against an immuno-inhibitory receptor.

12. A method of treating a proliferative disease or condition characterized by TROP2 positive cells in a patient in need thereof comprising administering to the patient an effective amount of the pharmaceutical composition of claim 7.

13. A compound of Formula Ic

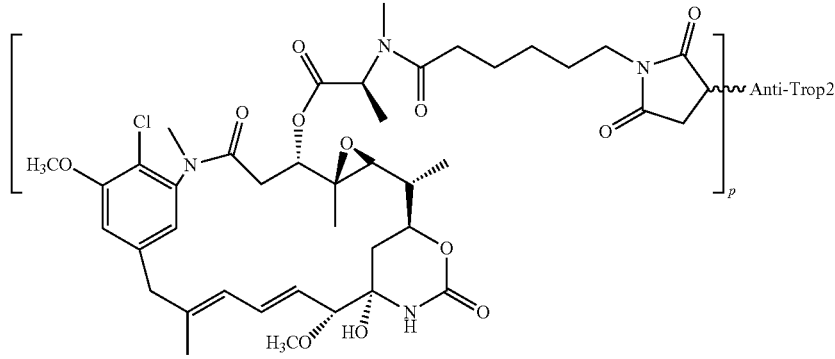

or a pharmaceutically acceptable salt or solvate thereof, wherein p is 2, and
anti-TROP2 is an anti-TROP2 antibody comprising a light chain comprising an amino acid sequence as shown in SEQ ID NO: 3, and a heavy chain comprising an amino acid sequence as shown in SEQ ID NO: 4.

14. The compound of claim 13, wherein the anti-TROP2 antibody has a fucose content of 0-5%.

15. A pharmaceutical composition comprising the compound of claim 13.

16. A method of treating a proliferative disease or condition characterized by TROP2 positive cells in a patient in need thereof comprising administering to the patient an effective amount of the compound of claim 13.

17. An antibody comprising a light chain comprising an amino acid sequence as shown in SEQ ID NO: 3, and a heavy chain comprising an amino acid sequence as shown in SEQ ID NO: 4.

18. The antibody of claim 17, wherein the antibody has a fucose content of 0-5%.

* * * * *